(12) United States Patent
Belliard

(10) Patent No.: US 8,721,645 B2
(45) Date of Patent: May 13, 2014

(54) BONE FIXING SYSTEM AND METHOD OF USE

(75) Inventor: Karl Pierre Belliard, La Membrolle sur Longuenee (FR)

(73) Assignee: Zimmer Spine, Bordeaux (FR)

( * ) Notice: Subject to any disclaimer, the term of this patent is extended or adjusted under 35 U.S.C. 154(b) by 152 days.

(21) Appl. No.: 13/248,749

(22) Filed: Sep. 29, 2011

(65) Prior Publication Data

US 2012/0022592 A1    Jan. 26, 2012

Related U.S. Application Data

(63) Continuation of application No. 12/682,001, filed as application No. PCT/EP2008/063682 on Oct. 10, 2008.

(30) Foreign Application Priority Data

Oct. 11, 2007   (EP) ..................................... 07301454

(51) Int. Cl.
*A61B 17/82* (2006.01)

(52) U.S. Cl.
USPC .............. 606/74; 606/263; 606/279; 606/324

(58) Field of Classification Search
USPC ............................ 606/74, 103, 277, 279, 324
See application file for complete search history.

(56) References Cited

U.S. PATENT DOCUMENTS

| 902,040 A | 10/1908 | Wyckoff |
| 1,346,940 A | 7/1920 | Collins |
| 2,049,361 A | 7/1936 | Johan |
| 4,570,618 A | 2/1986 | Wu |
| 5,030,220 A | 7/1991 | Howland |
| 5,304,178 A | 4/1994 | Stahurski |
| 5,356,412 A * | 10/1994 | Golds et al. ..................... 606/74 |
| 5,413,576 A | 5/1995 | Rivard |
| 5,449,361 A | 9/1995 | Preissman |

(Continued)

FOREIGN PATENT DOCUMENTS

| DE | 19716504 | 12/1998 |
| EP | 0780096 | 6/1997 |

(Continued)

OTHER PUBLICATIONS

Notice of Allowance issued in U.S. Appl. No. 11/877,160, mailed Oct. 31, 2011, 7 pages.

(Continued)

*Primary Examiner* — Jerry Cumberledge
(74) *Attorney, Agent, or Firm* — Seager, Tufte & Wickhem, LLC

(57) ABSTRACT

A bone fixing system useful for holding bone in position, and a method for installing the same are disclosed. The ends of a conformable ligature are passed around bones, bone grafts, tendons, plates, rods, fasteners, or other anatomical or implanted structures, and the like to form a loop extending from a first portion of a body. The ends of the conformable ligature are passed through the body and extend out a second portion of the body. The ends may be attached to a tensioning tool and a selected tension may be applied. A closure member may engage an engagement portion of the body to create a friction force to hold the conformable ligature in place without significant movement relative to the body.

11 Claims, 17 Drawing Sheets

(56) References Cited

U.S. PATENT DOCUMENTS

| | | | |
|---|---|---|---|
| 5,609,634 A | 3/1997 | Voydeville | |
| 5,649,927 A * | 7/1997 | Kilpela et al. | 606/74 |
| 5,667,508 A | 9/1997 | Errico | |
| 5,669,917 A | 9/1997 | Sauer et al. | |
| 5,683,404 A * | 11/1997 | Johnson | 606/151 |
| 5,702,399 A | 12/1997 | Kilpela et al. | |
| 5,720,751 A | 2/1998 | Jackson | |
| 5,772,663 A | 6/1998 | Whiteside et al. | |
| RE36,221 E | 6/1999 | Breard | |
| 5,935,133 A | 8/1999 | Wagner et al. | |
| 5,938,663 A | 8/1999 | Petreto | |
| 5,964,769 A | 10/1999 | Wagner et al. | |
| 6,053,921 A | 4/2000 | Wagner et al. | |
| 6,086,590 A | 7/2000 | Margulies et al. | |
| 6,099,527 A | 8/2000 | Hochschuler et al. | |
| 6,146,386 A | 11/2000 | Blackman et al. | |
| 6,179,838 B1 | 1/2001 | Fiz | |
| 6,228,096 B1 | 5/2001 | Marchand | |
| 6,241,740 B1 | 6/2001 | Davis et al. | |
| 6,277,120 B1 | 8/2001 | Lawson | |
| 6,299,613 B1 | 10/2001 | Ogilvie et al. | |
| 6,309,390 B1 | 10/2001 | Le Couedic et al. | |
| 6,352,557 B1 | 3/2002 | Ferree | |
| 6,391,030 B1 | 5/2002 | Wagner et al. | |
| 6,419,702 B1 | 7/2002 | Ferree | |
| 6,447,518 B1 | 9/2002 | Krause et al. | |
| 6,478,798 B1 | 11/2002 | Howland | |
| 6,514,255 B1 * | 2/2003 | Ferree | 606/263 |
| 6,527,794 B1 * | 3/2003 | McDevitt et al. | 606/232 |
| 6,547,770 B2 | 4/2003 | Carlsson et al. | |
| 6,547,790 B2 | 4/2003 | Harkey, III et al. | |
| 6,569,164 B1 | 5/2003 | Assaker et al. | |
| 6,569,171 B2 | 5/2003 | DeGuillebon et al. | |
| 6,605,091 B1 | 8/2003 | Iwanski | |
| 6,616,669 B2 | 9/2003 | Ogilvie et al. | |
| 6,656,179 B1 * | 12/2003 | Schaefer et al. | 606/267 |
| 6,656,185 B2 * | 12/2003 | Gleason et al. | 606/74 |
| 6,682,533 B1 | 1/2004 | Dinsdale et al. | |
| 6,689,140 B2 | 2/2004 | Cohen | |
| 6,695,852 B2 | 2/2004 | Gleason | |
| 6,723,335 B1 | 4/2004 | Moehlenbruck et al. | |
| 6,746,452 B2 | 6/2004 | Tuke et al. | |
| 6,773,438 B1 | 8/2004 | Knodel et al. | |
| 6,946,000 B2 | 9/2005 | Senegas et al. | |
| 7,481,828 B2 | 1/2009 | Mazda et al. | |
| 7,699,874 B2 | 4/2010 | Young | |
| 7,959,654 B2 | 6/2011 | Mazda et al. | |
| 8,403,930 B2 * | 3/2013 | Chico Roca | 606/74 |
| 2002/0116013 A1 | 8/2002 | Gleason et al. | |
| 2002/0198538 A1 | 12/2002 | Kortenbach et al. | |
| 2003/0195563 A1 * | 10/2003 | Foerster | 606/232 |
| 2004/0087979 A1 | 5/2004 | Field et al. | |
| 2004/0097942 A1 | 5/2004 | Allen et al. | |
| 2004/0138666 A1 | 7/2004 | Molz, IV et al. | |
| 2005/0070958 A1 | 3/2005 | Swayze et al. | |
| 2005/0085815 A1 | 4/2005 | Harms | |
| 2005/0131404 A1 | 6/2005 | Mazda | |
| 2005/0154403 A1 | 7/2005 | Sauer et al. | |
| 2005/0228375 A1 | 10/2005 | Mazda et al. | |
| 2005/0273983 A1 | 12/2005 | Mattchen | |
| 2006/0235387 A1 | 10/2006 | Peterman | |
| 2006/0235391 A1 | 10/2006 | Sutterlin, III | |
| 2007/0088359 A1 | 4/2007 | Woods et al. | |
| 2007/0299445 A1 | 12/2007 | Shadduck et al. | |
| 2008/0033557 A1 | 2/2008 | Pasquet et al. | |
| 2008/0125780 A1 | 5/2008 | Ferree | |
| 2008/0140133 A1 | 6/2008 | Allard et al. | |
| 2008/0208256 A1 | 8/2008 | Thramann | |
| 2009/0131985 A1 | 5/2009 | Mazda | |
| 2009/0138048 A1 | 5/2009 | Baccelli et al. | |
| 2009/0182379 A1 | 7/2009 | Baccelli et al. | |
| 2009/0326585 A1 | 12/2009 | Baccelli et al. | |
| 2011/0034956 A1 | 2/2011 | Mazda et al. | |
| 2011/0112581 A1 | 5/2011 | Clement | |
| 2011/0238118 A1 | 9/2011 | Baccelli et al. | |
| 2011/0238125 A1 | 9/2011 | Baccelli et al. | |
| 2012/0022591 A1 | 1/2012 | Baccelli et al. | |
| 2012/0289962 A1 * | 11/2012 | Hulliger et al. | 606/74 |
| 2012/0303065 A1 * | 11/2012 | Larroque-Lahitette et al. | 606/277 |

FOREIGN PATENT DOCUMENTS

| | | |
|---|---|---|
| EP | 1815812 | 8/2007 |
| FR | 522040 | 7/1921 |
| FR | 26156 | 9/1923 |
| FR | 2704745 | 11/1994 |
| FR | 2722088 | 1/1996 |
| FR | 2799948 A1 | 4/2001 |
| FR | 2817929 | 6/2002 |
| FR | 2867057 | 9/2005 |
| FR | 2870718 | 12/2005 |
| FR | 2890850 | 3/2007 |
| FR | 2890851 | 3/2007 |
| FR | 2897771 A1 | 8/2007 |
| GB | 2269753 | 2/2004 |
| JP | 2001299770 | 10/2001 |
| WO | WO9416635 A1 | 8/1994 |
| WO | 0154599 | 8/2001 |
| WO | WO0207621 A1 | 1/2002 |
| WO | WO0207622 A1 | 1/2002 |
| WO | 0209604 A1 | 2/2002 |
| WO | WO0209604 A1 | 2/2002 |
| WO | WO0217803 A2 | 3/2002 |
| WO | WO02051326 A1 | 7/2002 |
| WO | WO02071960 A1 | 9/2002 |
| WO | WO 03007829 A1 | 1/2003 |
| WO | WO03103519 A1 | 12/2003 |
| WO | WO2004010881 A1 | 2/2004 |
| WO | WO 2005020860 A3 | 3/2005 |
| WO | WO2005120277 A1 | 12/2005 |
| WO | WO2006034423 A2 | 3/2006 |
| WO | WO 2006106268 A3 | 10/2006 |
| WO | WO2006106246 | 12/2006 |
| WO | WO 2007023240 A3 | 3/2007 |
| WO | WO2007034112 A1 | 3/2007 |
| WO | WO2007036657 | 4/2007 |
| WO | WO2007099258 A2 | 9/2007 |

OTHER PUBLICATIONS

Notice of Allowance issued in U.S. Appl. No. 11/996,918, mailed Dec. 19, 2011, 9 pages.

English Translation of International Preliminary Report issued in International Patent Application No. PCT/FR2006/050898 on Patentability Chapter I dated Apr. 29, 2008, 6 pages.

English Translation of International Preliminary Report on Patentability Chapter I issued in International Patent Application No. PCT/FR2006/ 050909 dated Apr. 8, 2008, 5 pages.

English Translation of the Written Opinion of the International Search Authority issued in International Patent Application No. PCT/FR2006/ 050909 dated Apr. 2, 2008, 4 pages.

English Translation of the Written Opinion of the International Search Authority issued in International Patent Application No. PCT/FR2006/050898 dated Apr. 28, 2008, 5 pages.

European Search Report issued in European Patent Application No. EP 08305183 dated Mar. 19, 2009, 10 pages.

European Search Report issued in European Patent Application No. EP 08305326 dated Nov. 12, 2008, 3 pages.

European Search Report issued in European Patent Application No. EP 2052689 dated Apr. 15, 2008, 6 pages.

European Search Report issued in European Patent Application No. EP08305326 on Nov. 18, 2006, 3 pages.

French Preliminary Search Report and Written Opinion in French Patent Application No. FR200650609 dated Jun. 30, 2006, 5 pages.

International Search Report issued in International Patent Application No. WO2009053423 dated May 19, 2009, 4 pages.

International Search Report issued in International Patent Application No. PCT/EP2008/063682, mailed Nov. 24, 2008 3 pages.

International Search Report Issued in International Patent Application No. PCT/FR2006/050909, published as WO/2007/034112, dated Jan. 24, 2007, 3 pages.

(56) References Cited

OTHER PUBLICATIONS

Office Action issued in U.S. Appl. No. 10/521,914 mailed Dec. 29, 2006, 21 pages.
Office Action issued in U.S. Appl. No. 10/521,914 mailed Mar. 19, 2008, 7 pages.
Office Action issued in U.S. Appl. No. 10/521,914 mailed Jun. 16, 2006, 13 pages.
Office Action issued in U.S. Appl. No. 10/521,914 mailed Jul. 30, 2007, 13 pages.
International Search Report and Written Opinion issued in International Patent Application No. PCT/US2009/038977 mailed Jul. 22, 2009, 13 pages.
Korean Examination report issued in Korean Patent Application No. 1020057001238 mailed Feb. 23, 2010, 3 pages.
French Preliminary Search Report issued in French Patent Application No. FR0209317 dated Apr. 9, 2003, 1 page.
French Preliminary Search Report issued in French Patent Application No. FR0509629 mailed Jun. 9, 2006, 2 pages.
International Search Report issued in International Patent Application No. PCT/FR2003/02307 dated Jan. 2, 2004, 2 pages.
Australian Search Report issued in Australian Patent Application No. 2003267529 dated Nov. 15, 2007, 2 pages.
French Preliminary Search Report issued in French Patent Application No. FR0509570 dated Jun. 29, 2006, 2 pages.
International Search Report issued in International Patent Application No. PCT/FR2006/050898 dated Feb. 2, 2007, 2 pages.
Written Opinion issued in International Patent Application No. PCT/US2009/038977 mailed Feb. 24, 2010, 7 pages.
European Search Report issued in European Patent Application No. 07 301 454.0, mailed Sep. 25, 2008, 8 pages.
Partial European Search Report issued in European Patent Application No. 07 301 483.9, completed Apr. 15, 2008, mailed Apr. 23, 2008, 6 pages.
European Search Report and Search Opinion issued in European Patent Application No. 07 301 483.9, completed Apr. 15, 2008, mailed Jul. 10, 2008, 10 pages.
International Search Report and Written Opinion issued in International Patent Application No. PCT/EP2008/064344, completed Jan. 16, 2009, mailed May 19, 2009, 11 pages.
International Search Report and Written Opinion issued in International Patent Application No. PCT/EP2008/062791, completed Nov. 18, 2008, mailed Dec. 4, 2008, 10 pages.
French Preliminary Search Report issued in French Patent Application No. 0757814, issued May 22, 2008, 2 pages.
International Preliminary Report on Patentability issued in International Patent Application No. PCT/ EP2008/062791, Mar. 30, 2010, 7 pages.
International Preliminary Report on Patentability issued in International Patent Application No. PCT/ EP2008/063682, Apr. 13, 2010, 8 pages.
International Preliminary Report on Patentability issued in International Patent Application No. PCT/ EP2008/064344, Apr. 27, 2010, 8 pages.
International Preliminary Report on Patentability issued in International Patent Application No. PCT/US2009/038977, May 27, 2010, 12 pages.
French Preliminary Search Report issued in French Patent Application No. FR 0405611, dated Jan. 12, 2005, 2 pages.
International Search Report issued in International Patent Application No. PCT/FR2005/001280, Nov. 7, 2005, 3 pages.
Written Opinion issued in International Patent Application No. PCT/FR2005/001280, Nov. 25, 2006, 5 pages.
International Search Report issued in International Patent Application No. PCT/EP2008/064344, published as WO/2008/053423, mailed May 19, 2009, 5 pages.
International Search Report and Written Opinion issued in International Patent Application No. PCT/EP2008/063682, mailed Nov. 24, 2008, 11 pages.
International Search Report and Written Opinion issued in International Patent Application No. PCT/FR2006/050909, published as WO/2007/034112, mailed Jan. 24, 2007, 10 pages.
Office Action issued in U.S. Appl. No. 12/358,748, mailed Sep. 15, 2010, 7 pages.
Office Action issued in U.S. Appl. No. 11/877,160, mailed Nov. 26, 2010, 10 pages.
Office Action issued in U.S. Appl. No. 11/996,918, mailed Feb. 14, 2011, 12 pages.
Office Action issued in U.S. Appl. No. 12/059,634, mailed Feb. 15, 2011, 15 pages.
Office Action issued in U.S. Appl. No. 12/408,592, mailed Feb. 18, 2011, 17 pages.
Notice of Allowance issued in U.S. Appl. No. 12/358,748, mailed Feb. 23, 2011, 5 pages.
Office Action issued in U.S. Appl. No. 11/877,160, mailed Apr. 12, 2011, 12 pages.
Office Action issued in U.S. Appl. No. 12/059,634, mailed Jun. 22, 2011, 15 pages.
European Search Report issued in European Patent Application No. EP08305124.3, Oct. 24, 2008, 4 pages.
Office Action issued in U.S. Appl. No. 11/996,918, mailed Aug. 17, 2011, 11 pages.
Notice of Allowance issued in U.S. Appl. No. 12/375,265, mailed Aug. 25, 2011, 10 pages.
Office Action issued in U.S. Appl. No. 12/408,592, mailed Sep. 22, 2011, 24 pages.
Office Action issued in U.S. Appl. No. 12/059,634, mailed Oct. 5, 2011, 12 pages.

* cited by examiner

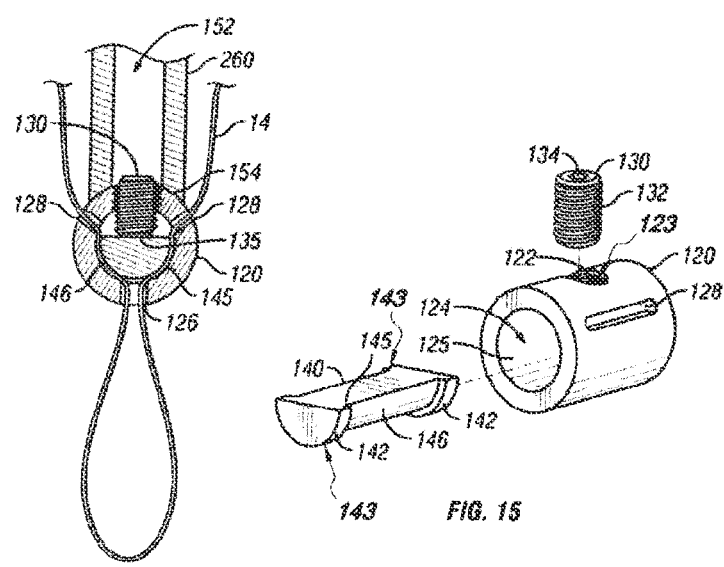
FIG. 14
FIG. 15
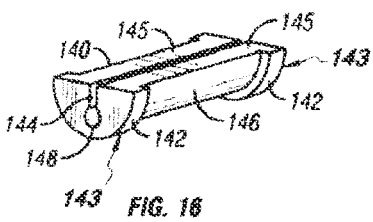
FIG. 16

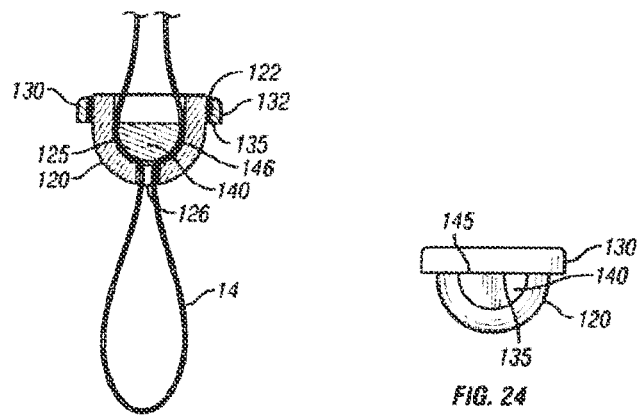
FIG. 23
FIG. 24
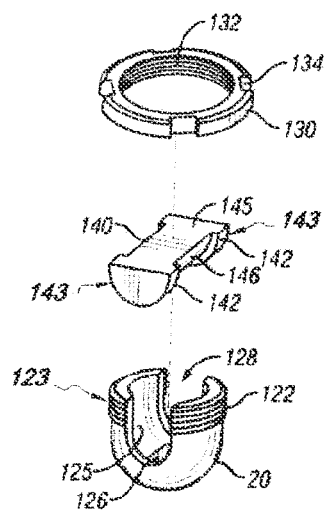
FIG. 25

BONE FIXING SYSTEM AND METHOD OF USE

This application is a continuation of U.S. patent application Ser. No. 12/682,001, filed Apr. 7, 2010, entitled "BONE FIXING SYSTEM AND METHOD OF USE," which is a national stage application, filed under 35 U.S.C. 371, of International Patent Application No. PCT/EP2008/063682, filed Oct. 10, 2008, which claims priority to European Patent Application No. EP 07301454, filed Oct. 11, 2007, and which relates to U.S. patent application Ser. No. 10/521,914, filed Jan. 20, 2005, now U.S. Pat. No. 7,481,828, entitled "VERTEBRAL FIXING SYSTEM," which is a national stage application of and claims priority to International Patent Application No. PCT/FR03/02307, filed Jul. 22, 2003, which claims priority to French Patent Application No. 02 09317, filed Jul. 23, 2002. This application relates to U.S. patent application Ser. No. 12/854,753, filed Aug. 11, 2010, now U.S. Pat. No. 8,323,319, entitled "VERTEBRAL FIXING SYSTEM," which is a continuation of U.S. patent application Ser. No. 12/358,748, filed Jan. 23, 2009, now U.S. Pat. No. 7,959,654, entitled "VERTEBRAL FIXING SYSTEM," which is a continuation of U.S. patent application Ser. No. 10/521,914 and U.S. patent application Ser. No. 12/375,265, filed Jan. 27, 2009, now U.S. Pat. No. 8,172,843, which is a national stage application of and claims priority to International Patent Application No. PCT/FR2006/050898, filed Sep. 18, 2006, entitled "VERTEBRAL FIXING SYSTEM." All applications listed herein are incorporated by reference in their entireties.

TECHNICAL FIELD

This disclosure relates generally to systems and methods for fixing bone. In particular, embodiments of the disclosure may be helpful for holding bones, rods, or other structures in a desired configuration or in a particular relative position.

BACKGROUND

One field of application for the disclosure is holding bones in a relative position, for example to aid in healing of breaks or positioning bones in the treatment of scoliosis or otherwise to correct abnormal curvatures of the spine. Other bone deficiencies and abnormalities may also benefit from embodiments of the present disclosure.

The spine is formed of superposed vertebrae, normally aligned along a vertebral axis, from the lumbar vertebrae to the cervical vertebrae, each having a posterior wall from which projects a spinous process and two lateral edges from the walls of which there project ribs and/or transverse processes. If the spine of a person has abnormal curvature, the vertebrae are typically inclined relative to one another and relative to said vertebral axis. The lateral edges of the vertebrae on one side are therefore closer together and form a concave shape while the lateral edges on the other side are farther apart and form a convex shape.

In order to straighten the vertebral column as a remedy for this situation, the lateral edges of the vertebrae on the concave side can be moved away from one another and supported at distances from one another substantially equivalent to the distances between the lateral edges on the other side. Devices known in the art to hold the vertebrae relative to one another include screws that are inserted into the vertebrae or hooks that are inserted along the internal wall of the spinal canal and rods adapted to connect the screws or hooks.

When using a hook and rod system, pairs of hooks are generally inserted into each vertebra, one on each side, near the pedicle. The hooks typically have heads that project from the posterior wall of the vertebra, one on each side of the spinous process. The heads can be tulip-shaped and adapted to receive a rod that is immobilized by a nut screwed onto the head and contacting the rod. The heads of the hooks situated on either side of the spinous process can then be connected together and fixed in position by two rods approximately parallel to one another and to the axis of the spine.

However, using such hooks can be difficult because their use increases the risk that the physician (or other operative) might contact and potentially damage the spinal cord that extends along the center of the spinal canal (which can result in paralysis of the patient).

Using a screw and rod system reduces this risk, but has other drawbacks. The screws typically have tulip-shaped heads and are inserted in pairs into the pedicles on each side of the spinous process on the posterior wall of the vertebrae. The screws therefore constitute fixing points on the vertebrae for holding the vertebrae in a fixed position relative to one another. However, the screws are inserted into the pedicles of the vertebrae, which in some cases are small or have deteriorated and can be damaged or do not provide sufficient purchase to permanently hold the screw.

SUMMARY

A bone fixing system and method of use for holding a bone, portions of a bone or multiple bones in a fixed relative position that provides advantages over conventional bone fixing systems and methods of use. In one embodiment, the bone fixing system and method of use provides the ability to hold bones in a fixed relative position when it is not possible or practicable to insert screws into the vertebrae and when using hooks may increase dangers to the patient.

One embodiment of the disclosure is directed to a bone fixing system for holding a bone in a position including a conformable ligature with a first end and a second end and a loop portion, a blocking body having a loop passage, an exit passage, an engagement portion, a closure member for engagement with the engagement portion of the blocking body, and a compression member having a first surface. In some embodiments, the closure member engages with the blocking body so that the first surface of the compression member contacts the conformable ligature to create a friction force between the conformable ligature and the blocking body. In some embodiments, the loop portion passes through the loop passage and the first and second ends extend from the exit passage. In some embodiments, the friction force is great enough to hold the conformable ligature in place without significant (or in some cases without any) movement relative to the blocking body. The exit passage can include a first exit passage and a second exit passage and further wherein the first end passes through the first exit passage and the second end passes through the second exit passage.

The blocking body can include a compression member opening for receiving the compression member and the compression member can have a second surface for contacting the closure member. In some embodiments, at least one extension maintains the position of the compression member in the blocking body. In some embodiments, said extension protrudes from the outer surface of the compression member and is arranged to abut against the blocking body for maintaining the position of the compression member in the blocking body. In other embodiments, said extension protrudes from the inner surface of the blocking body and is arranged to abut against the compression member for maintaining the position of the compression member in the blocking body. In some embodiments, the closure member comprises a bottom surface for contact with the second surface of the compression member. In some embodiments, engagement of the closure member biases the bottom surface of the closure member with the second surface of the compression member to create a friction force between the conformable ligature and the blocking body.

The engagement portion can be a threaded engagement portions that includes external threads, while the closure member can be an internally threaded closure member where the closure member engages with the engagement member by rotation to engage the sets of threads. In one embodiment the threaded engagement portion can be a threaded hole sized to receive a closure member that is a screw.

In the previously described and/or alternative embodiments, the blocking body can be a U-shaped channel defined by two upwardly extending arms. In some embodiments, the blocking body includes a first portion and a second portion, wherein the first portion is connected with the second portion via a hinge. In some embodiments, the first or second portion comprises the compression member. In some embodiments, engagement of the closure member to the blocking collapses the first portion relative to the second portion to create the friction force between the conformable ligature and the blocking body.

In one embodiment, the bone fixing system includes a tensioning tool with a tool body having an attachment point for connecting to first and second ends of the conformable ligature, a longitudinal member for advancement in the tool body, and a distal end for engagement with the blocking body. In some embodiments of the bone fixing system and method of use, the tensioning tool tensions one or more ends of the conformable ligature when the distal end is engaged with the blocking body, one or more ends of the conformable ligature are attached to the tool body, and the longitudinal member is advanced through the tool body.

Yet another embodiment is directed to a method for holding a bone in a position, comprising the steps of passing a conformable ligature around one or more structures in a body, passing first and second ends of the conformable ligature through a loop passage in a blocking body to form a loop extending from a first portion of the blocking body, passing the first and second ends out the exit passage of the blocking body to extend from a second portion of the blocking body, applying tension to the conformable ligature, and engaging the closure member in the engagement portion to hold the conformable ligature in place without significant movement relative to the blocking body.

In some embodiments, a blocking body comprises a loop passage, an exit passage, a threaded portion, a threaded closure member for engagement with the threaded portion, and a compression member having a first surface. In some embodiments, advancing the longitudinal member comprises tensioning the conformable ligature to position a structure relative to another structure. In some embodiments, a structure comprises a bone, a bone fastener, a tendon, a bone graft, a plate, or a rod.

These, and other, aspects of the disclosure will be better appreciated and understood when considered in conjunction with the following description and the accompanying drawings. The following description, while indicating various embodiments of the disclosure and numerous specific details thereof, is given by way of illustration and not of limitation. Many substitutions, modifications, additions or rearrangements may be made within the scope of the disclosure, and the disclosure includes all such substitutions, modifications, additions or rearrangements.

BRIEF DESCRIPTION OF THE FIGURES

FIG. 14 depicts a cross-sectional end view of one embodiment of a bone fixing system.

FIG. 15 depicts an exploded perspective view of one embodiment of a blocking body.

FIG. 16 depicts a perspective view of one embodiment of a compression member.

FIG. 23 depicts a cross-sectional end view of one embodiment of a bone fixing system.

FIG. 24 depicts a side view of one embodiment of a blocking body.

FIG. 25 depicts an exploded view of one embodiment of a blocking body.

DETAILED DESCRIPTION

Figure 1:
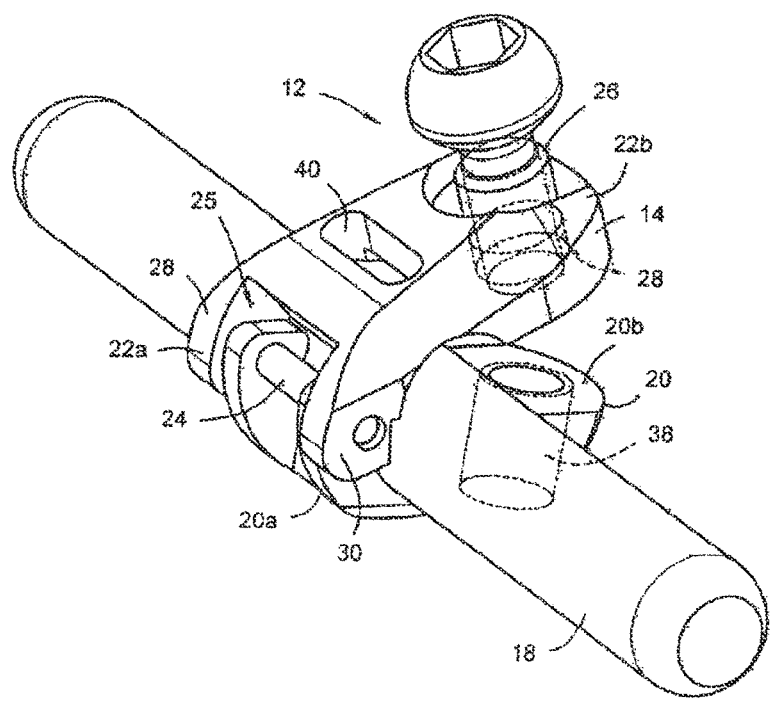
FIG. 1 is a fragmentary diagrammatic perspective view showing a vertebral fixing system of the disclosure and a rod.

The disclosure and the various features and advantageous details thereof are explained more fully with reference to the non-limiting embodiments that are illustrated in the accompanying drawings and detailed in the following description. Descriptions of well known starting materials, processing techniques, components and equipment are omitted so as not to unnecessarily obscure the disclosure in detail. Skilled artisans should understand, however, that the detailed description and the specific examples, while disclosing preferred embodiments of the disclosure, are given by way of illustration only and not by way of limitation. Various substitutions, modifications, additions or rearrangements within the scope of the underlying inventive concept(s) will be apparent to those skilled in the art after reading this disclosure.

A bone fixing system may be installed in a patient to hold or fix one structure in a selected relation with one or more other structures. As used herein, the term structure may refer to bones, portions of bones, or bone implants, as well as rods, elongated members, plates, or other implanted man-made devices. Among other methods, a bone fixing system as described herein may be installed using a minimally invasive surgery (MIS) procedure. In one embodiment, the bone fixing system and method of use may include instruments and bone fixing components for maintaining one or more structures in a selected alignment.

Components of bone fixing systems in accordance with the disclosure may be made of materials including, but not limited to, titanium, titanium alloys, stainless steel, ceramics, and/or polymers. Some components of a bone fixing system may be autoclaved and/or chemically sterilized. Components that may not be autoclaved and/or chemically sterilized may be made of sterile materials. Components made of sterile materials can be used with other sterile components during assembly of a bone fixing system.

Embodiments of bone fixing systems disclosed herein are useful in repairing broken bones, correcting curvatures of the spine and for other surgical procedures that hold structures (e.g., bones) in a fixed relative position. Embodiments of the bone fixing system and method of use disclosed herein can be particularly useful for minimally invasive surgery (MIS) procedures, which can reduce trauma to soft tissue due to the relatively small incision made in a patient. For example, a surgical procedure may be performed through a 2 cm to 4 cm incision formed in the skin of the patient. Dilators, a targeting needle, and/or a tissue wedge may be used to provide access to structures without the need to form a larger incision with a scalpel through muscle and other tissue. A minimally invasive surgery (MIS) procedure may reduce an amount of postoperative pain felt by a patient as compared to invasive procedures. A minimally invasive procedure may also reduce recovery time for the patient as compared to invasive procedures. In some embodiments, the natural flexibility of skin and soft tissue may be used to limit the length and/or depth of an incision or incisions needed during the procedure. Minimally invasive procedures may provide limited direct visibility in vivo.

Bone fixing systems may be used to correct problems due to spinal injury, deformity, or disease. For example, various embodiments of a bone fixing system may be used from the C1 vertebra to the sacrum to correct spinal problems. For example, a bone fixing system may be implanted posterior to the spine to maintain distraction between adjacent vertebral bodies in a lumbar portion of the spine. Various embodiments of a bone fixing system may be used to correct orthopedic deficiencies. Embodiments of the disclosure may be useful for holding tendons, bones, or muscles during the healing process and may be implanted using MIS procedures and thus it is in this context that embodiments of the disclosure may be described. It will be appreciated, however, that embodiments of the systems and methods of the present disclosure may be applicable for stabilizing other areas of the body.

FIG. 1 shows one embodiment of a bone fixing system, specifically a vertebral fixing system 10 of the disclosure mounted on a rod 18. The vertebral fixing system comprises a connecting part 12 having two longitudinal members, of which a first longitudinal member 22 extends between a first end 22a and a second end 22b and a second longitudinal member 20 extends between a first end 20a and a second end 20b. The two longitudinal members 22 and 20 are pivoted together at their first ends 20a and 22a for the purposes of mounting the system. The first end 22a of the longitudinal member 22 has a notch 25 with two opposite edges 28 and 30 and between which the first end 20a of the other longitudinal member 20 may be inserted. A pivot pin 24 passes through the two first ends 20a and 22a and is free to rotate in at least one of said ends 20a and/or 22a. The second end 22b of the first longitudinal member 22 includes a bore 28 into which a screw 26 may be inserted. The second end 20b of the second longitudinal member 20 comprises a thread 38 which is aligned with said bore 28 when the two longitudinal members are disposed facing each other, with the result that the screw 26 may be screwed into said thread 38 in order to drive the second ends 20b and 22b of the two longitudinal members 20 and 22 towards each other. The consequences of screwing said screw 26 into the thread 38, thereby forming the adjustable locking means, are explained in more detail hereinafter. FIG. 1 also shows a first orifice 40 through which a ligature may be stretched. The method of connecting said ligature to said connecting part is described with reference to FIG. 2.

Figure 2:
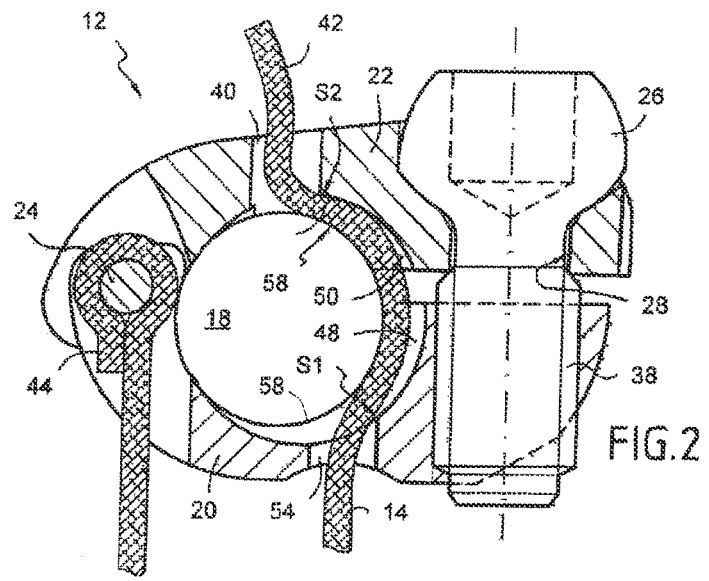
FIG. 2 is a diagrammatic view in vertical section of the subject matter of the disclosure mounted on a rod.

FIG. 2 shows the connecting part 12 consisting of the first longitudinal member 22 and the second longitudinal member 20, said longitudinal members 22 and 20 pivoting about the pin 24 that joins them. The adjustable locking means consisting of said screws 26 passing through the bore 28 and screwed into the thread 38 to immobilize said connecting part 12 relative to the rod 18 and fix in position a portion of a ligature 14 shown in part in FIG. 2.

The ligature 14 consists of an elongate flexible member capable of conforming to the contour of the parts that it must connect.

Figure 4:
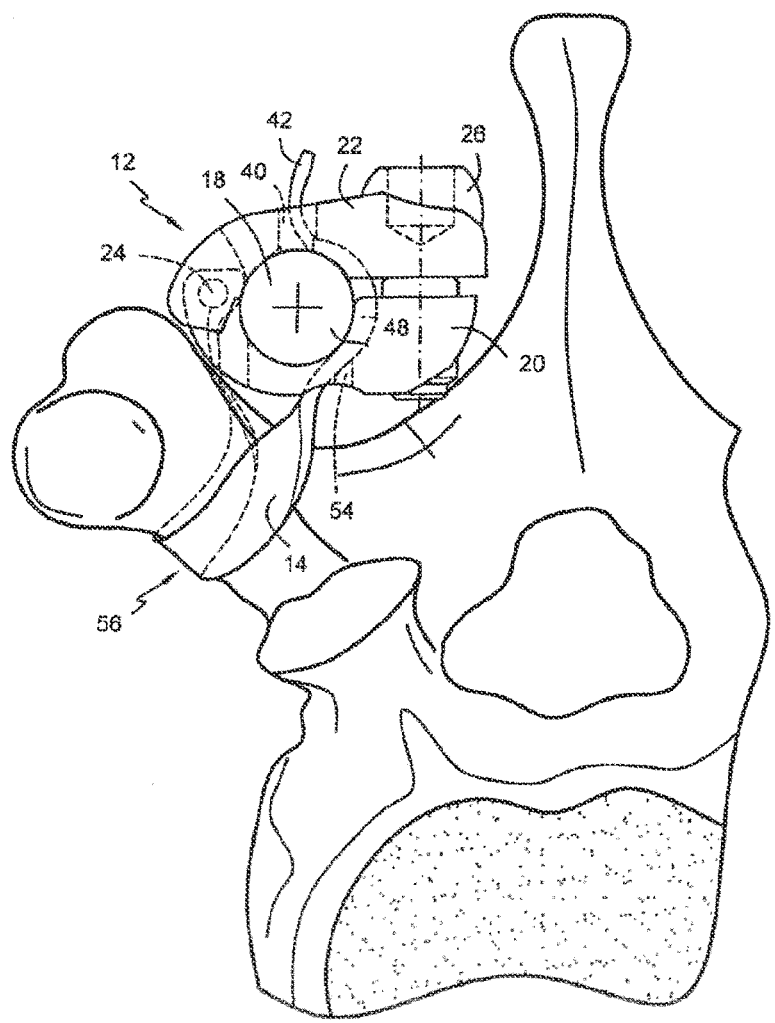
FIG. 4 is a diagrammatic view in elevation of the subject matter of the disclosure mounted on a vertebra.

The ligature 14 has a first end 44 that is ligated around the pin 24 and a free second end 42 that is inserted into a passage 48 between the rod 18 and the internal walls 50 and 52 of the longitudinal members 22 and 20 and the external wall of the rod 18. As shown in FIG. 2, the second longitudinal end 20a includes a second orifice 54 through which said ligature 14 passes. Moreover, as shown in FIG. 4, the ligature 14 may be formed into a loop 56 in which the transverse process is trapped. In some embodiments, the ligature 14 may also trap the rib.

Figure 3:
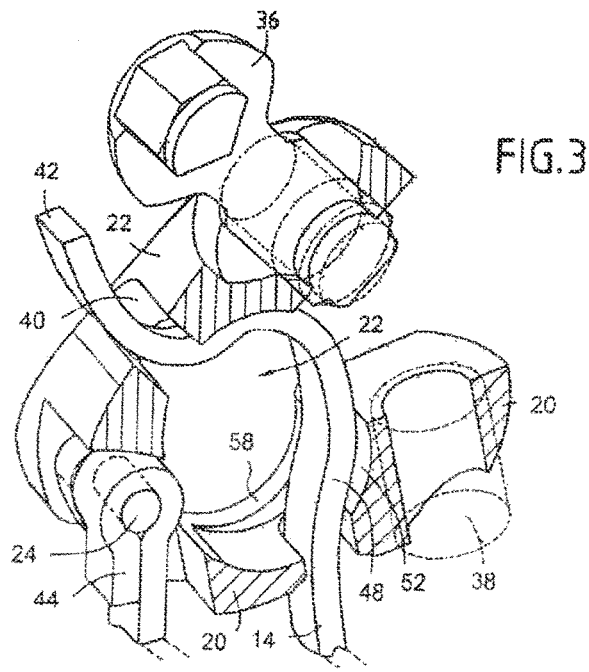
FIG. 3 is a diagrammatic perspective view in section of the subject matter of the disclosure.

As shown in FIG. 3, which shows the second longitudinal member 20, the middle part has a first portion through which said ligature 14 passes and a second portion 58 adapted to bear directly on the rod 18. In some embodiments, the passage 48, which is symmetrical inside the first longitudinal member 20, is produced by a groove formed in each of the two facing faces of the middle parts of the longitudinal members 22 and 20.

In some embodiments, the first portion of the middle part forms an edge with cylindrical symmetry and the corresponding second portion of the middle part 58 of the first longitudinal member 22 forms a substantially cylindrical space 60 into which said rod 18 is inserted.

FIG. 2 shows that the second portion 58 of the middle part comes into contact with the rod 18 and is adapted to bear on top of it and the first portion presses the free second end of said ligature 14 against the rod 18. The adjustable locking means therefore drive the longitudinal members 22 and 20 forcibly against the rod 18 and simultaneously against the ligature 14, which is also forcibly pressed against the rod 18.

In some embodiments, as shown in FIG. 2, the passage 48 has a section S1 in the vicinity of the orifice 54 greater than the section S2 in the vicinity of the first orifice 40, the section of said passage 48 decreasing progressively in the direction from the second orifice 54 to the first orifice 40. The ligature 14 is therefore progressively compressed around a portion of the rod 18 with a pressure that increases in the direction from the second orifice 54 towards the first orifice 40.

FIG. 4 shows a vertebral fixing system of the disclosure mounted on a vertebra having a transverse process. This figure shows again the rod 18 and the two longitudinal members 22 and 20 that grip it and press a portion of the ligature 14 against said rod 18.

In FIG. 4, the flexible ligature 14 consists of a flexible strip of substantially constant width and thickness whose first end is ligated to the pin 24, the ligature 14 surrounding the transverse process of the vertebra being inserted through the connecting part 12. The section of the flexible strip 14 is substantially rectangular so that, the pin 24 and the rod 18 being substantially perpendicular to the transverse process, the ligature 14 has to be partly twisted in order to insert it into the passage 48 and between the pin 24 and the point at which it contacts the transverse process. The connecting part 12 is fixed in position against the posterior wall of the vertebra despite these partially twisted portions, the ligature 14 being forcibly tensioned by stretching the free second end 14.

The ligature 14 is advantageously made from a flexible material such as polyester that may be lightly crushed locally to immobilize it with a clamping effect.

One aspect of the disclosure relates to a spine straightening assembly comprising a plurality of vertebral fixing systems conforming to the present disclosure and mounted on a plurality of successive vertebrae, on all the transverse processes of one lateral wall thereof, and connected to a single rod that is disposed substantially parallel to said spine. The transverse processes of a portion of the spine can therefore be connected together by a single longitudinal rod, to fix them in position relative to each other, by means of the above vertebral fixing system.

Figure 5:
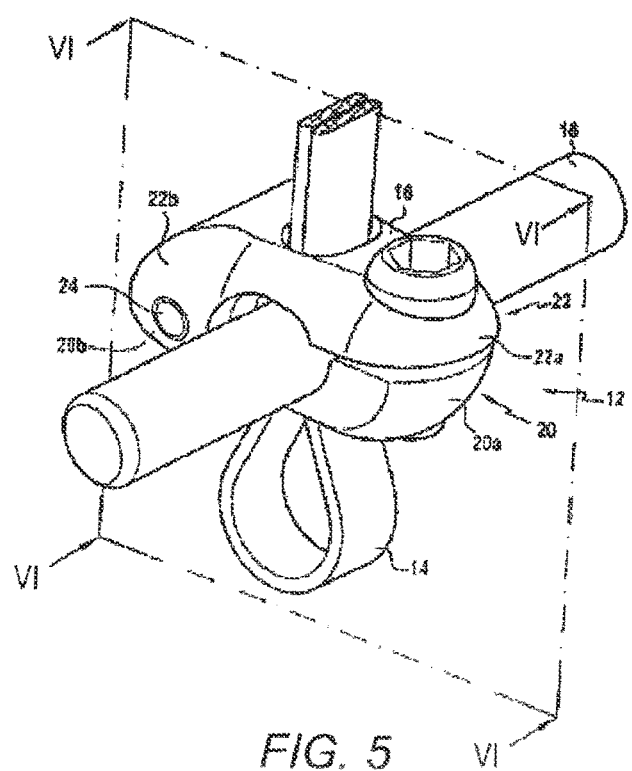
FIG. 5 is a perspective view of a first embodiment of a vertebral fixing system.

In some embodiments, flexible ligature 14 may not be ligated around pin 24 or otherwise fixed to connecting part 12. As shown in FIG. 5, in one embodiment, a vertebral fixing system comprises a connecting part 12, a flexible ligature 14, and adjustable locking means 16. The flexible ligature 14 is of elongate shape and is capable of matching the outline of the parts it is to connect together. In this figure, there can also be seen the rod 18 that is to be secured to the vertebra by means of the vertebral fixing system. In the first embodiment, the connecting part 12 is constituted by two longitudinal elements given respective references 22 and 20, each having a first end 22a, 20a and a second end 22b, 20b.

Figure 6A:
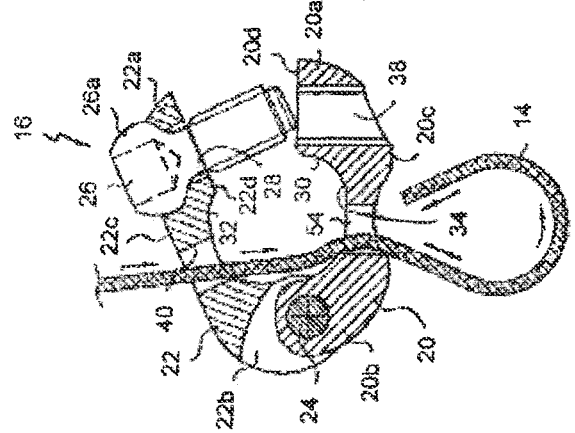
FIGS. 6A, 6B, and 6C are vertical section views of the fixing system showing the use of said system as shown in FIG. 5.

In FIG. 6A, the longitudinal elements 22 and 20 are hinged to each other at their first ends 22a, 20a about a pivot pin 24.

In the embodiment described, the locking means are constituted by a screw 26 having a head 26a that is engaged in a bore 28 formed in the second end 22b of the longitudinal element 22. The second end 20b of the longitudinal element 20 is pierced by a tapped bore 38 for co-operating with the threaded shank 26b of the screw 26. Each longitudinal element 20, 22 has an outside face 20c, 22c and an inside face 20d, 22d. The longitudinal elements 20 and 22 are mounted in such a manner that the inside faces 20d, 22d of the longitudinal elements face each other. The inside faces 20d, 22d of the longitudinal elements 20 and 22 have respective mutually-facing recesses 30 and 32, each of substantially semi-cylindrical shape. The recesses 30 and 32 define walls 34 and 36 which are ruled surfaces having generator lines parallel to the pivot axis 24. Finally, slots 54 and 40 cause the bottoms of the recesses 30 and 32 to communicate with the outside faces 20c and 22c of the longitudinal elements 20 and 22. As explained below, the recesses 30 and 32 are for receiving the rod 18 together with a strand of the ligature 14, the slots 54 and 40 serving to pass the ligature 14.

Figure 6B:
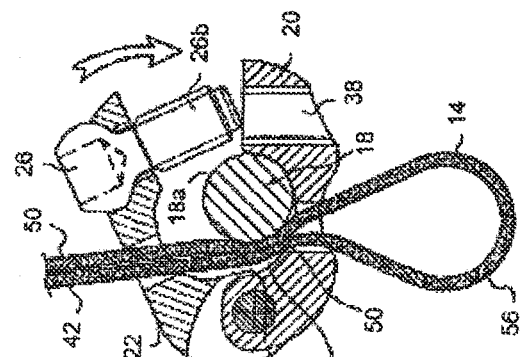
Figure 6C:
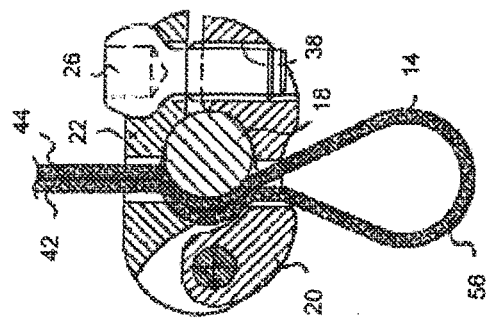

With reference to FIGS. 6A, 6B and 6C, there follows an explanation of how the fixing system is used.

In FIG. 6A, there can be seen the longitudinal elements 20 and 22 in the spaced-apart position, a position in which the locking means 16 are not active, the threaded shank 26b of the screw 26 not being engaged in the bore 38. The ligature 14 is engaged in the slots 54 and 40 of the longitudinal elements against one portion of the inside wall 34, 36 of the recesses 30 and 32. The rod 18 is then introduced into the recess 30 of the longitudinal element 20 so that the two strands 42 and 44 of the ligature 14 are disposed between the inside wall of the recesses 30 and 32 and the side face 18a of the rod 18. These two surfaces define a passageway 48 for passing the ligature 14 and having portions 42 and 44 of the ligature 14 placed therein.

As shown in FIG. 6B, the portions 42 and 44 of the ligature 14 define a portion of the ligature 14 that forms a loop that extends beyond the outside face 20c of the longitudinal element 20, and also two free portions 42 and 44 that extend beyond the outside face 22c of the longitudinal element 22. When the longitudinal elements 20 and 22 are spaced apart as shown in FIG. 6B, the ligature 14 can slide freely along the passageway 48. Once the ligature 14 is placed around the transverse process or a rib or indeed a portion of the posterior arc of a vertebra, the surgeon engages the threaded shank 26b of the screw 26 in the tapped bore 38, causing the longitudinal element 22 to come progressively closer to the longitudinal element 20. This approach simultaneously reduces the section of the passageway 48 in which the portions 42 and 44 of the ligature 14 are engaged and simultaneously introduces a certain coefficient of friction between the ligature and respectively the rod 18 and the walls of the recesses 30 and 32. Nevertheless, it is still possible for the surgeon to extract traction on the free ends 42 and 44 of the ligature 14 until sufficient tension is obtained in the ligature around the vertebral process. Once the tension in the ligature is sufficient for providing appropriate fastening, the surgeon finishes off tightening the screw 26 in the tapped bore 38, thus locking the longitudinal elements 20 and 22 together. Advantageously, the portions 42 and 44 of the ligature 14 are pinched between the rod 18 and the wall of the recesses 30 and 32.

In this locking position, the rod 18 is thus secured to the ligature 14 via the connecting part 12.

Figure 7:
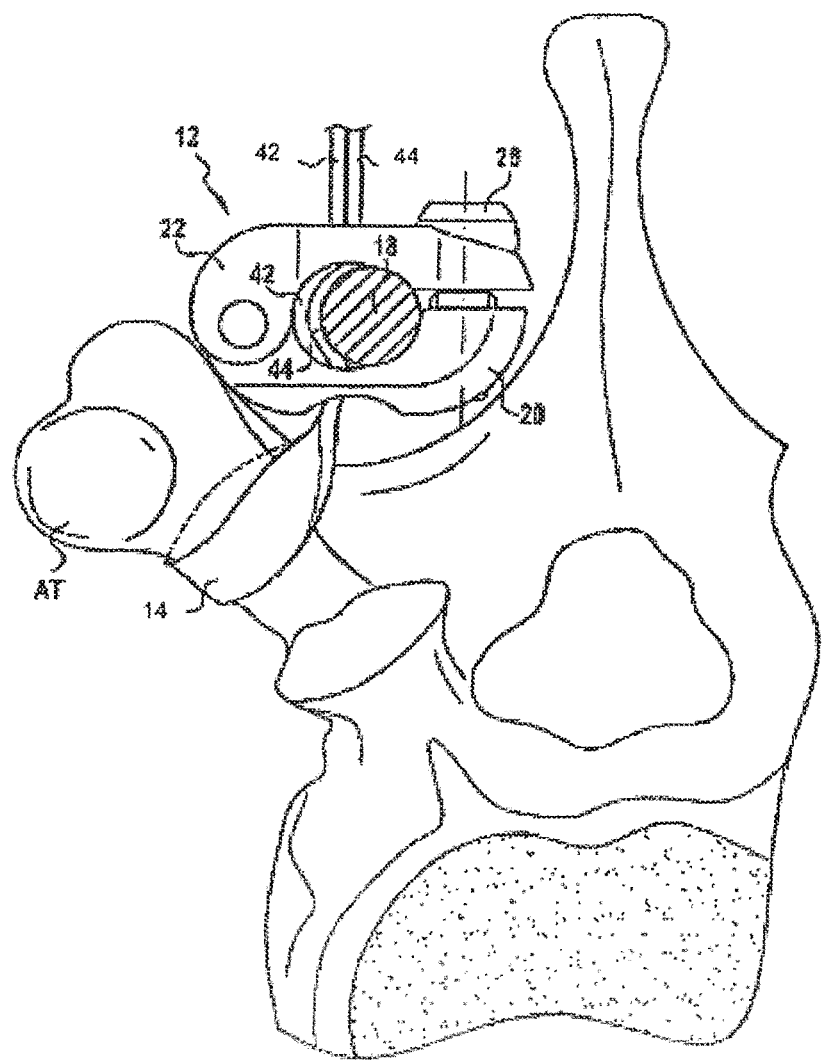
FIG. 7 is a face view showing the FIG. 5 fixing system put into place on a vertebra.
Figure 8:
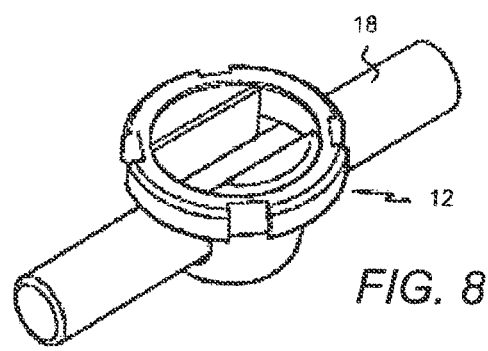
FIG. 8 is a perspective view of a second embodiment of the fixing system, the ligature not being shown.
Figure 9:
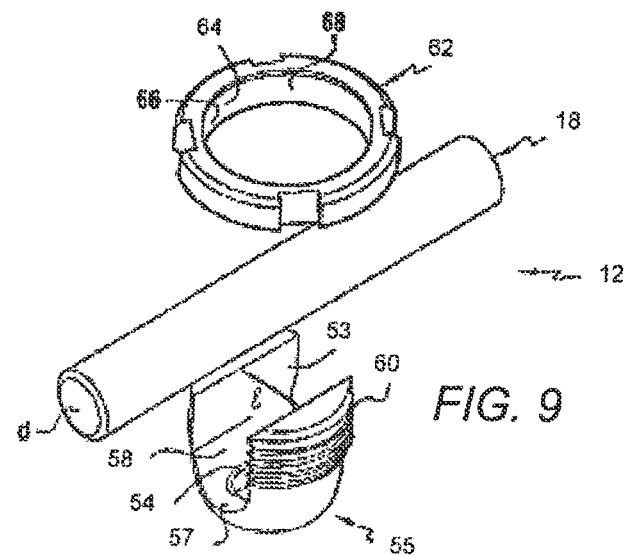
FIG. 9 is an exploded view of the connection device of FIG. 8.

Advantageously, because the surgeon exerts traction only on the free ends 42 and 44 of the ligature 14, there is no risk of jamming between the ligature 14 and the bottom face of the transverse process or of the rib, thus guaranteeing that effective fastening is provided with the transverse process or the rib or indeed a portion of the posterior arc of a vertebra. FIG. 7 depicts a face view where reference AT identifies the transverse process.

In the above description, both of the portions 42 and 44 of the ligature 14 are disposed in the recesses 30 and 32 on the same side of the rod 18. In some embodiments, the portions 42 and 44 of the ligature 14 may be placed on opposite sides of the rod 18. Under such circumstances, it should be considered that the outside face 18a of the rod 18 and the inside walls of the recesses 30 and 32 define two passageways, respectively for passing each of the portions 42 and 44 of the ligature 14.

FIGS. 8 to 13B depict various view of one embodiment of the fixing system. In these figures, there can be seen the rod 18, the connecting part 12, and the flexible ligature 14.

In this embodiment, the connecting part 12 is constituted by a part 55 that is generally U-shaped. The inside wall of this part 55 is constituted by a bottom 57 of substantially semi-cylindrical shape and by two substantially plane portions 53 and 54 that correspond to the two limbs of the part 55. The width of the recess 58 formed in the part 55 is substantially equal to the diameter of the rod 18. On its outside face 59 which is circularly symmetrical about a longitudinal axis of the part 55, there is provided a thread 60 occupying its upper portion. The thread 60 is located entirely above the rod 18 when it is put into place in the recess 58. The thread 60 is designed to co-operate with a clamping ring 62 that constitutes the adjustable locking means. This ring has a slightly frustoconical bore 64 with an inside face 66 that carries tapping 68.

In some embodiments, when the ring 62 is screwed tight on the threaded portion 60 of the part 55, it deforms the limbs of the part 55 elastically, thereby pinching and clamping strands of the ligature 14 between the rod 18 and the inside wall(s) of the recess 58, in a manner explained below.

Figure 11:
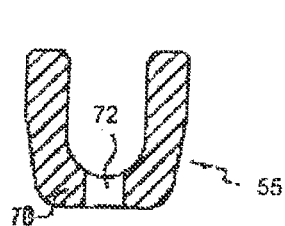
FIG. 11 is a section view on line XI-XI of FIG. 10.
Figure 10:
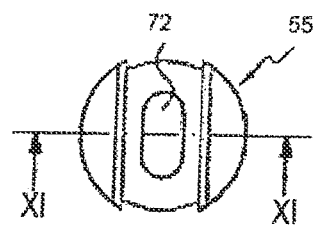
FIG. 10 is a plan view of a portion of the FIG. 9 connection device.

As shown in FIGS. 10 and 11, the part 55 includes in its bottom 70 a passage 72 for passing the ligature 14 in a manner explained below.

Figure 12:
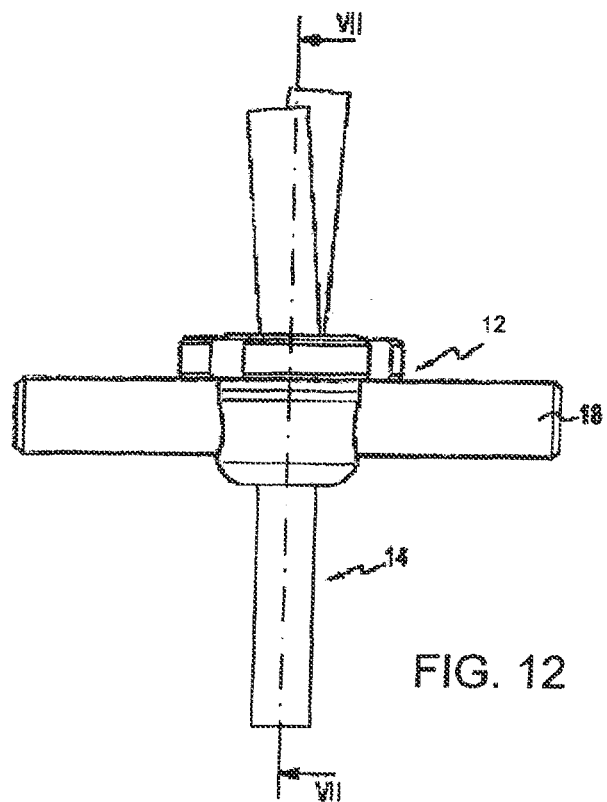
FIG. 12 is a face view of the fixing system of the second embodiment.
Figure 13A:
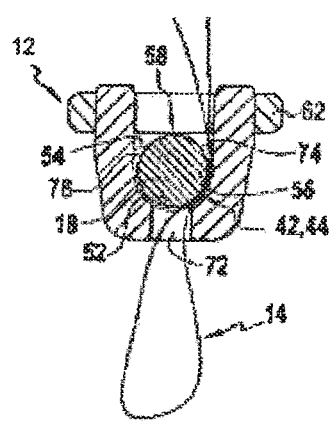
FIGS. 13A and 13B are section views on line VII-VII of FIG. 12 showing two ways in which the flexible ligature can be put into place.
Figure 13B:
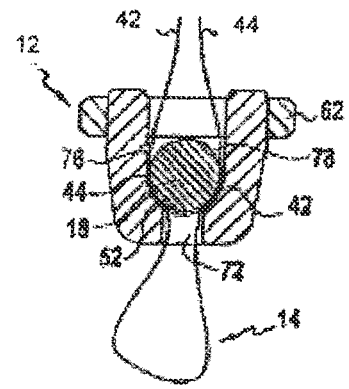

With references to FIGS. 12, 13A, and 13B, there follows a description of two different ways of putting the flexible ligature 14 into place inside the connecting part 12 in the second embodiment. The side wall of the rod 18 and the inside wall of the recess 58 of the part 55 potentially define two passageways 74 and 76 for passing the middle strands of the flexible ligature 14. In the configuration shown in FIG. 13A, only the passageway 74 is used. Thus, both intermediate portions 42 and 44 of the flexible ligature 14 are disposed in the passage 74.

In the configuration shown in FIG. 13B, the middle portions 42 and 44 of the flexible ligature 14 are disposed respectively one in each of the passageways 74 and 76, i.e. on either side of the rod 18. Advantageously, the free ends of the ligature 14 are accessible for exerting the desired traction in order to obtain suitable clamping on the spinous process prior to locking the clamping ring 62 on the part 55.

One advantage to this type of embodiment may be the ability to avoid making two longitudinal parts constituting a kind of clamp hinged on the pin 24. In some embodiments, the locking means are constituted by an element that is distinct from the connecting part and that is removable therefrom. In some embodiments, the locking means co-operate with the connecting part by screw engagement. It is thus possible to adjust accurately the dimensions of the ligature-passing passageway(s) as defined by the connecting part and the rod. In an initial stage, the coefficient of friction between the coefficient of the ligature and secondly the rod and the connecting part can be adjusted. In the final stage, very effective clamping of the ligature is obtained between the rod and the locking part.

In some embodiments, including for example the embodiments shown in FIGS. 14-39, rod 18 may not be needed in order for the bone fixing system to effectively hold a bone in a relative position. The embodiments of the bone fixing system 100 shown in FIGS. 14-39 can include conformable ligature 14 and blocking body 120, which may include compression member 140. In these embodiments that do not require the use of rod 18, the conformable ligature 14 may be passed around one or more bones, tendons, muscles, rods, plates, screws, or other structures in a body and passed through loop passage 126 in blocking body 120 to form a loop extending from a first portion of blocking body 120 and a first end and a second end of conformable ligature 14 may be passed out one or more exit passages 128 in blocking body 120 to extend in a free configuration from a second portion of blocking body 120. Thus, although conformable ligature 14 may, in some uses, pass around rod 18 to capture rod 18 in a loop portion, rod 18 is not necessary for bone fixing system 100 to hold a bone in a secure position.

With reference to FIGS. 14-38, in embodiments that do not require the use of rod 18 to hold a structure in a relative position, bone fixing system 100 may include compression member 140 having a first surface 146 for contact with conformable ligature 14 and for cooperating with inside surface 125 of blocking body 120 to form a passageway for one or more ends of conformable ligature 14. Compression member 140 may be inserted into blocking body 120 before conformable ligature 14 is passed through blocking body 120. In some embodiments, closure member 130 may engage with engagement portion 123 of blocking body 120 before inserting compression member 140 and/or passing conformable ligature 14 through blocking body 120.

In other embodiments that do not require the use of rod 18 to hold a structure in a relative position, bone fixing system 100 may include closure member 130 for engagement with engagement portion 123 of blocking body 120 and for contact with compression member 140 so that advancing closure member 130 into blocking body 120 biases compression member 140 onto conformable ligature 14. Closure member 130 may be advanced into blocking body 120 for biasing compression member 140 against conformable ligature 14 to create a friction force between conformable ligature 14 and blocking body 120. A friction force between conformable ligature 14 and blocking body 120 may hold conformable ligature 14 in place without significant movement relative to blocking body 120. In some embodiments, closure member 130 may be advanced into blocking body 120 for impinging conformable ligature 14 between compression member 140 and blocking body 120 to prevent any relative movement.

Advantageously, the use of compression member 140 in these embodiments enable bone fixing system 100 to be used in circumstances in which rod 18 may be undesirable or unnecessary. Another advantage of the embodiments illustrate in FIGS. 14-38 is the ability for the surgeon to more easily see conformable ligature 14 as it is passed through various passages in the bone fixing system. Another advantage to this embodiment is the reduced size of blocking body 120 over prior art devices that couple to a rod. In particular, the use of compression member 140, particularly having a hemispherical profile, can reduce the height and overall profile of blocking body 120.

FIG. 14 depicts a cross-sectional view of a portion of one embodiment of bone fixing system 100 useful for holding a bone in a position without requiring rod 18. Bone fixing system 100 of FIG. 14 includes blocking body 120 with compression member 140 and closure member 130, ligature 14, and tensioning tool 250. Blocking body 120 of FIG. 14 includes closure member passage 123 for receiving closure member 130 and loop passage 126 and exit passages 128 for receiving ligature 14 through blocking body 120 (e.g., as shown). As shown in FIG. 14, ligature 14 has been passed through blocking body 120 such that each end 14 of ligature 14 extends out of one of exit passage 128 and ligature 14 passes through loop passage 126 to form ligature loop portion. In some embodiments, ligature 14 may have a round profile, which can often provide the highest strength per unit of cross-sectional area of ligature 14, enable passing ligature through small openings, and/or reduce the area of contact with a structure. As shown in FIG. 14, ligature 14 may have a wide, flat (or approximately flat) profile which may distribute forces over a larger area, provide higher strength, and/or prevent rolling (e.g. as compare to a round profile). Compression member 140 includes first surface 146 for cooperating with inner surface 125 of blocking body 120 to form a passageway between loop passage 126 and exit passages 128. As shown in FIG. 14, closure member 130 includes threads 132 for engaging threads 122 in engagement portion 123 of blocking body 120 and bottom surface 135 for contact with compression member 140. As shown in FIG. 14, closure member 130 has been engaged with threads 122 in blocking body 120 and bottom surface 135 contacts compression member 140 such that ligature 14 is held in place relative to blocking body 120 due to compression in the passageways formed by first surface 146 and inner surface 125 between loop passage 126 and exit passages 128. As shown in FIG. 14, bone fixing system 100 includes tensioning tool 250 having central passage 152 for passage of ends 14 of ligature 14 and distal end 154 for contact with blocking body 120.

As shown in FIG. 14 (and FIG. 15), blocking body 120 may be manufactured with inner surface 125 for cooperating with first surface 146 of compression member 140 to form a space through which conformable ligature 14 passes and for contacting with a portion of conformable ligature 14 to hold conformable ligature 14 in position. In some embodiments, inner surface 125 may be manufactured with a grooved, knurled, or otherwise textured surface to aid in holding conformable ligature 14 in place. Inner surface 125 of blocking body 120 may be coated, layered, or otherwise treated to aid in holding conformable ligature 14 in place. In some embodiments, inner surface 125 may allow one-way passage of conformable ligature 14 through blocking body 120, for example, by manufacturing inner surface 125 with an asymmetric saw-tooth profile to allow passage of conformable ligature 14 through blocking body 120 in a first direction but to resist movement in the opposite direction.

As shown in FIG. 14, loop passage 126 is located along the arclength opposite (i.e., facing) first surface 146 of compression member 140 positioned in blocking body 120, but it should be understood that loop passage 126 could be positioned at other places around blocking body 120. As shown in the embodiment of FIG. 14, exit passages 128 are located on opposing portions of blocking body 120 and each is located higher than the uppermost portion of compression member 140 when positioned in blocking body 120. However it should be understood that exit passages 128 can be located at other positions around blocking body 120. In various embodiments, loop passage 126 and exit passages 128 may be circular, oval, elliptical, or other shape, may be symmetric or asymmetric, and may be oriented such that conformable ligature 14 may enter or exit blocking body 120 at an angle, normal, or substantially tangential to a portion of blocking body 120. In alternative embodiments, there may only be a single exit passage 128 through which both ends 14 of ligature 14 pass.

As shown in FIG. 14, tensioning tool 250 (discussed in further detail below) has distal end 154 for detachable engagement with a portion of blocking body 120. In some embodiments, distal end 154 of longitudinal member 260 may have passage 152 for accessing closure member 130. As shown in FIG. 14, distal end 154 may be curved for engagement with a portion of blocking body 120 having a generally curved profile.

In some uses, ligature 14 may have one or both ends passed around a structure in the body. Both ends of ligature 14 may be inserted in loop passage 126 to form a loop around the structures. Compression member 140 may be inserted in compression member opening 124. Ligature 14 may be passed through the passageway formed between first surface 146 of compression member 140 and inner surface 125 of blocking body 120. Ends of ligature 14 may be passed out one or more exit passages 128. Closure member 130 may be inserted in engagement portion 123 to engage threads 122. Ends of ligature 14 may be connected to tensioning tool 250, such as tensioning tool 250 shown in FIG. 39. Ligature 14 may be tightened, and closure member 130 may be inserted in engagement portion 123 and advanced until closure member 130 contacts compression member 140. Advancing compression member 140 creates a friction force between ligature 14 and blocking body 120. The friction force may be great enough to impinge ligature 14 relative to blocking body 120 or may be enough to resist movement of ligature 14 relative to blocking body 120.

FIG. 15 depicts an exploded perspective view of the embodiment of blocking body 120 shown in FIG. 14, including compression member 140 and closure member 130. As shown in FIG. 15, blocking body 120 includes engagement portion 123 having threads 122 for receiving closure member 130, and compression member opening 124 through which compression member 140 may be inserted to "side-load" compression member 140 within blocking body 120. As shown in the embodiment of FIG. 15, closure member 130 includes tool portion 134 and thread 132 and compression member 140 includes first surface 146, second surface 145, and flanges 142.

As shown in FIG. 15, blocking body 120 can include compression member openings 124 on either side of blocking body 120 for insertion of compression member 140. In the embodiment of FIG. 15, compression member opening 124 has a constant diameter, while in alternative embodiments opening 124 may have a first diameter large enough to accommodate flanges 142 and a second diameter smaller than flange 142 but large enough to seat compression member 140. Compression member 140 can be inserted, positioned, and/or removed from blocking body 120. In various embodiments, compression member 140 may be short enough to fit inside blocking body 120, compression member 140 may be substantially the same length as blocking body 120, or compression member 140 may extend some distance beyond blocking body 120. Advantageously, compression member 140 enables embodiments of the bone fixing system 100 to operate in areas of the body or in situations in which a rod may be difficult or undesirable. An advantage to blocking body 120 having compression member opening 124 oriented for side-loading compression member 140 is the ability to adjust the positioning of compression member 140 after closure member 130 has engaged engagement portion 123.

Extensions 143 (such as flanges 142) of compression member 140 can operate to prevent compression member 140 from shifting or moving out of position once closure member 130 has engaged engagement portion 123 of blocking body 120. Extensions 143 protrude from the outer surface of compression member 140 and are arranged to abut against blocking body 120 for maintaining the position of the compression member in the blocking body. In operation, closure member 130 will contact compression member 140 to hold ligature 14 substantially in place when ligature 14 has been positioned to hold a bone or other structure in a relative position. In some embodiments, when compression member 140 has a longitudinal shape along a main axis, extensions 143 may be located near the axial ends of compression member 140 and protrude radially from the outer surface of compression member 140. For instance, extension 143 may be a flange 142, a portion of flange, a pin, etc. In some embodiments, extensions 143 may extend around the entire arclength of first surface 146 of compression member 140, such as flanges 142 depicted in FIG. 15, while in other embodiments, extensions 143 may extend around a portion of the arclength of first surface 146. In some embodiments, a radius of extension 143 may allow insertion or removal of compression member 140 in a first orientation and may prevent removal or insertion in a second orientation. For example, in some embodiments, extensions 143 may have a radius to enable compression member 140 to be inserted into blocking body 120 when compression member 140 is rotated to a first angle, while preventing compression member 140 from being removed when compression member 140 is rotated (e.g., 90 degrees) from the first angle. In some embodiments, compression member 140 may have a variable radius.

As shown in the embodiment of FIG. 15, first surface 146 of compression member 140 can form a passageway in cooperation with inner surface 125 of blocking body 120 for passing ligature 14 and for contacting conformable ligature 14. In some embodiments, first surface 146 may be knurled, grooved, or otherwise machined, may be coated, layered, or otherwise treated for contact with conformable ligature 14, and/or may allow one-way passage of conformable ligature 14 through compression member 140 (e.g., having an asymmetric saw-tooth profile for allowing passage of conformable ligature 14 past compression member 140 in a first direction but resisting passage in an opposite direction).

Various mechanisms can be used to allow closure member 130 to engage engagement portion 123 of blocking body 120. In some embodiments, closure member 130 has helically wound thread 132 and can be advanced in blocking body 120 through engagement passage 123 by rotating closure member 130 to engage threads of engagement portion 123 of blocking body 120. In some embodiments, tool portion 134 on closure member 130 can be a hex shaped receiving are that would allow a surgeon to use a hex tool to engage and rotate closure member 130 so that threads 132 engage with the threads of engagement portion 123. In some embodiments, closure member 130 may have a sawtooth profile or other profile for ratcheting closure member 130 into blocking body 120. Those of ordinary skill in the art will recognize a variety of other mechanisms (some of which will be described herein) for engaging closure member 130 with engagement portion 123 in order to enable closure member 130 to contact compression member 140 and secure in place ligature 14.

Advantages to embodiments of bone fixing systems 100 such as the one depicted in FIGS. 14 and 15 include the curved profile of blocking body 120, which can result in an overall lower profile and/or in less stress on surrounding tissue based on friction contact.

FIG. 16 depicts a perspective view of an alternative embodiment of compression member 140 of FIGS. 14 and 15 having longitudinal slot 144 and stress reducer 148. In some embodiments, compression member 140 may have a length and width such that when compression member 140 is positioned inside blocking body 120, first surface 146 is in contact with inner surface 125 of blocking body 120 (or first surface 146 is in contact with conformable ligature 14 which is in contact with inner surface 125 of blocking body 120, for example as shown in FIG. 14). In various embodiments, compressing on second surface 145 may bias first surface 146 against inner surface 125 and the radius of curvature of first surface 146 may effectively change some amount, based at least in part on the length and depth of longitudinal slot 144. One advantage to compression member 140 having longitudinal slot 144 is the capability to adjust the compressive force exerted by compression member 140 on ligature 14. In addition to the length and depth of longitudinal slot 144, the amount that the radius of curvature can change can depend on the compression force applied to second surface 147, the shape of inner surface 125, the deformability of any coating, layer, a machined feature of inner surface 125 or first surface 146, the thickness of conformable ligature 14, or the original shape of first surface 146. As shown in the embodiment of FIG. 16, longitudinal slot 144 can include stress reducer 148, which can advantageously prevent or reduce the likelihood of compression member 140 cracking or other material failure due to a change in curvature of first surface 146. While other shapes can be employed, stress reducer 148 may be generally circular or other non-angular shape to prevent the build-up of stresses associated with bending forces. The radius and position of stress reducer 148 may be based on the material used for compression member 140, the radius of curvature of first surface 146, the depth and width of longitudinal slot 144, the anticipated compression force applied to second surface 147, or the length of compression member 140.

Figures 17, 18:
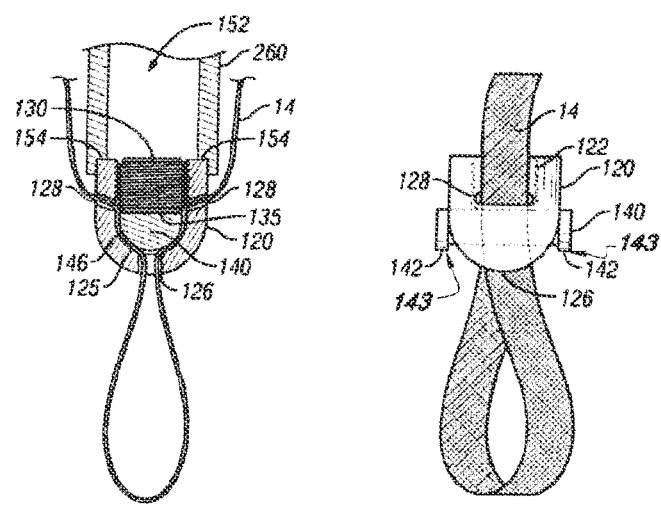
FIG. 17 depicts a cross-sectional end view of one embodiment of a bone fixing system.
FIG. 18 depicts a side view of one embodiment of a bone fixing system.
Figure 19:
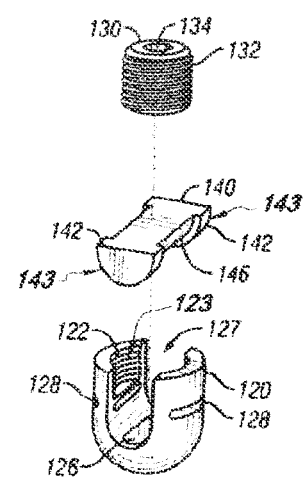
FIG. 19 depicts an exploded view of one embodiment of a blocking body.

FIGS. 17-19 illustrate another embodiment of the bone fixing system 100. FIG. 19 is a perspective view of this embodiment of blocking body 120, in which compression member 140 and closure member 130 may be top-loaded or side-loaded into blocking body 120 via U-shaped channel 127. In this embodiment, blocking body 120 is shown to include two upwardly extending walls forming a generally U-shaped channel 127. Compression member 140 is shown with a similar "dual cylinder" shape as the compression member 140 of FIG. 16 (in fact, the compression member of FIG. 16 can be used in the FIG. 17 embodiment) with first surface 146 and flanges 142. As shown in FIG. 18, compression member 140 may extend some distance beyond blocking body 120 with extensions 143 on compression member 140 designed to prevent compression member 140 from moving laterally once compression member 140 is positioned in blocking body 120. As shown in the FIG. 18 embodiment, extensions 143 may be located exterior to blocking body 120 (while in alternative embodiments, extensions 143 may be located interior to blocking body 120).

Compression member 140 can be placed within channel 127 with surface 146 contacting inner wall 125 at the bottom of channel 127. Closure member 130 may be inserted into channel 127 (e.g., by engaging the exterior threads on the body of closure member 130 with the interior threads 122 of channel 127) for engaging engagement portion 123. Advancing closure member 130 down channel 127 (e.g., rotating closure member 130) can force compression member 140 against ligature 14 to hold ligature 14 in place without significant movement (or with complete impingement) relative to blocking body 120.

FIG. 17 shows a cross-sectional view of this embodiment of bone fixing system 100 using the blocking body 120 of FIG. 19 in which compression member 140 is either side or top-loaded into blocking body 120. As shown in FIG. 17, conformable ligature 14 may be passed through loop passage 126 in blocking body 120 to form a loop extending from blocking body 120 and first and second ends may be passed out one or more exit passages 128 to extend from a second portion of blocking body 120. In order to use the bone fixing system 100 to hold a bone in position, compression member 140 may be inserted in blocking body 120 after conformable ligature 14 has been passed through blocking body 120. Closure member 130 may be engaged to engagement portion 123 of blocking body 120 after conformable ligature 14 has been passed through blocking body 120 and after compression member 140 has been positioned in blocking body 120. Engaging closure member 130 in engagement portion 123 of blocking body 120 prevents all or significant movement of conformable ligature 14 relative to blocking body 120.

As shown in FIG. 17, exit passages 128 can be positioned higher than first surface 146 of compression member 140 in order to provide a longer passage between first surface 146 of compression member 140 and inner surface 125 of blocking body 120 to provide a higher friction coefficient or reduced point stresses on conformable ligature 14, blocking body 120, and/or compression member 140. In alternative embodiments, exit passages 128 may be positioned near engagement portion 123 such that closure member 130 may contact conformable ligature 14. In various embodiments, closure member 130 may impinge a portion of conformable ligature 14. As shown in FIG. 17, exit passages 128 may be located on blocking body 120 such that when distal end 154 of tensioning tool 250 engages blocking body 120, first and second ends of ligature 14 are external of distal end 154. However, it should be understood that exit passages 128 may be located at a number of locations on the blocking body 120 and relative to tensioning tool 250. Distal end 154 of tensioning tool 250 may engage a portion of blocking body 120 to enable a surgeon to tension conformable ligature 14 in order to hold a bone or structure in position. In various embodiments, distal end 154 of tensioning tool 250 may be flanged for engaging blocking body 120. Tensioning tool 250 may include passage 152 along the entire length of tensioning tool 250 for accessing closure member 130 or passage 152 may extend a selected length of tensioning tool 250.

FIG. 18 depicts a side view of this embodiment of bone fixing system 100 where conformable ligature 14 passes through loop passage 126 to form a loop extending from a first portion of blocking body 120, and further passes through a passage formed by compression member 140 and blocking body 120, and passes out both exit passages 128 (though ligature 14 could in various embodiments pass both ends through a single exit passage 128). FIG. 18 illustrates the flanges 142 extending outside of blocking body 120.

As described, closure member 130 may be top-loaded into blocking body 120 for the embodiments of FIGS. 17-19. One advantage to top-loading closure member 130 and compression member 140 is that closure member 130 may be integrated with compression member 140 to form a unitary piece, which reduces the number of components that the surgeon has to implant during surgery. In various embodiments, closure member 130 may be connected to compression member 140 by a pin (not shown) to form a unitary piece. In some embodiments, closure member 130 may rotate while compression member 140 does not rotate. One advantage to this unitary closure member/compression member embodiment is that compression member 140 may apply only compression forces to ligature 14. In contrast, if compression member 140 rotates inside blocking body 120, torsion may be applied to ligature 14.

Figures 20, 21:
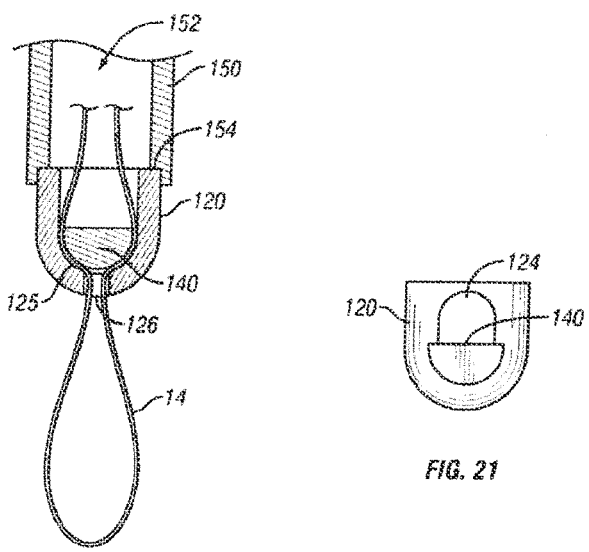
FIG. 20 depicts an exploded view of one embodiment of a bone fixing system.
FIG. 21 depicts a side view of one embodiment of a blocking body.
Figure 22:
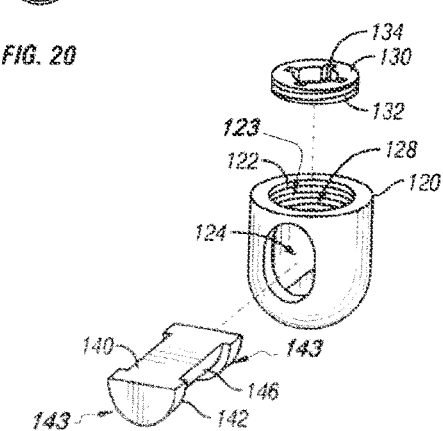
FIG. 22 depicts an exploded view of a portion of a blocking body.

FIGS. 20-22 depict yet another embodiment of bone fixing system 100 in which conformable ligature may be passed around one or more bones, tendons, muscles, rods, plates, screws, or other structures in the body, and then passed through loop passage 126 in blocking body 120 to form a loop extending from a first portion of blocking body 120. Ligature 14 can then be passed through a passageway formed by first surface 146 of compression member 140 and inner surface 125 of blocking body 120, and passed out through the center of blocking body 120 to extend out of blocking body 120 so that ends 14 of ligature 14 can be in a free configuration. Tensioning tool 250 may have a central passage 152 to allow first end and second end of ligature 14 to pass through.

FIG. 21 depicts a side view of a portion of one embodiment of blocking body 120, in which compression member 140 may be side-loaded through compression member opening 124 into blocking body 120. As shown, blocking body 120 of FIG. 21 has a similar shape to the blocking body 120 of FIG. 19, except that the FIG. 21 embodiment of blocking body 120 encloses compression member 140 (as opposed to the "open" top of the blocking body 120 of FIG. 19). Thus, in the FIG. 21 embodiment, compression member 140 may be pre-loaded into blocking body 120 or even manufactured to be permanently enclosed within blocking body 120. In an alternative embodiment, compression member 140 and/or extensions 143 may be manufactured with dimensions such that once compression member 140 is inserted in blocking body 120, the position of compression member 140 may be altered but compression member 140 may not be removed from blocking body 120. In other words, in the embodiment shown in FIG. 21, compression member 140 may be moved around inside blocking body 120, but may not be removed. In various embodiments, blocking body 120 may be manufactured with compression member opening 124 having a first set of dimensions and after compression member 140 is inserted into blocking body 120 through opening 124, the size of opening 124 may be altered (e.g., by adding material or altering the shape of blocking body 120 at opening 124) to reduce opening 124 dimension to prevent removal of compression member 140. Alternatively, compression member 140 may be manufactured having a first set of dimensions, inserted into opening 124 of blocking body 120, and then altered, such as by adding material, to increase the dimensions of compression member 140 to prevent removal of compression member 140. In various embodiments, compression member 140 may be compression fit or sweat-locked through opening 124 into blocking body 120. In another embodiment, blocking body 120 may be manufactured with two upwardly extending walls, compression member 140 may be inserted in a channel formed by the two walls, and material may be added to convert the channel into opening 124.

FIG. 22 depicts an exploded perspective view of the embodiment of blocking body 120 of FIGS. 20 and 21 in which compression member 140 may be side-loaded into blocking body 120 and closure member 130 may threadably engage engagement portion 123 of blocking body 120. A tool may engage with tool portion 134 for rotating closure member 130 to engage external threads 132 on closure member 130 with internal threads 122 in blocking body 120. Tool portion 134 of closure 130 can be hollow to enable one or more ends of conformable ligature 14 to pass through and extend out exit passage 128.

FIGS. 23-25 show another embodiment of a bone fixing system 100 having an alternate closure mechanism and exit passage. FIG. 23 depicts a cross sectional end view of bone fixing system 100 in which conformable ligature 14 may be passed through loop passage 126 in blocking body 120 to form a loop extending from a first portion of blocking body 120, through a passage formed by first surface 146 of compression member 140 and inner surface 125 of blocking body 120, and extend out through exit passage 128. As shown in FIGS. 23 and 25, in this embodiment, ring-style closure member 130 may have internal threads 132 for engaging external threads 122 on blocking body 120. This type of embodiment will provide the advantage of allowing the surgeon to see conformable ligature 14 as it passes through loop passage 126 in blocking body 120 and to see compression member 140 as it is positioned in blocking body 120.

FIG. 24 depicts a side view of the FIG. 23 embodiment in which bottom surface 135 of closure member 130 is in contact with second surface 145 of compression member external to blocking body 120, and in this embodiment bottom surface 135 of closure member 130 contacts second surface 145 at extensions 143 of compression member 140. An advantage to this type of embodiment is the ability for the surgeon to see the engagement between threads 132 on closure member 130 with threads 122 on blocking body 120. As shown in FIG. 24, tool portions 134 of closure member 130 may be positioned on an exterior portion of closure member 130. An advantage to this type of embodiment is the ability for a tool (not shown) to engage tool portions 134 exterior to distal end 154 (not shown) engaged with a portion of blocking body 120. This exterior engagement can provide a superior tightening mechanism to engage closure member 130 with blocking body 120 in certain embodiments.

FIG. 25 depicts an exploded perspective view of the FIG. 24 view with the various portions of blocking body 120 separated prior to engagement of closure member 130 onto blocking body 120. An advantage to this embodiment is the reduced number of passages, which may reduce the time needed to implant the system.

Figure 26:
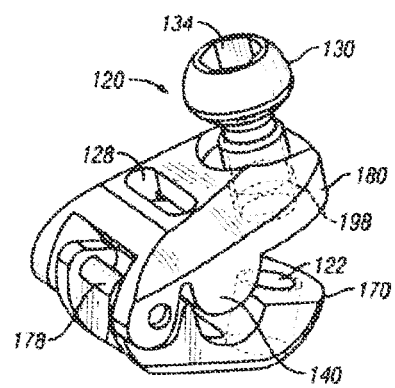
FIG. 26 depicts a perspective view of one embodiment of a blocking body.
Figure 27:
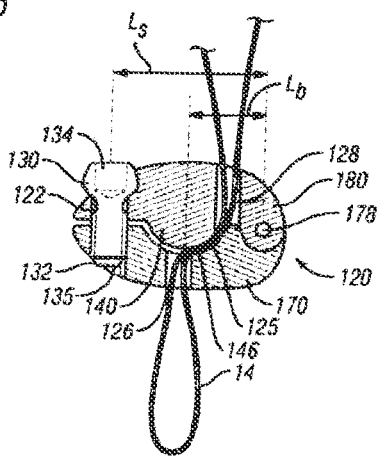
FIG. 27 depicts a cross-sectional side view of one embodiment of a bone fixing system.
Figure 28:
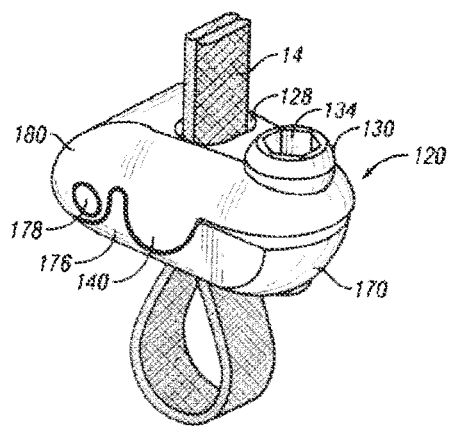
FIG. 28 depicts a perspective view of one embodiment of a bone fixing system.

FIGS. 26-28 illustrate an alternative embodiment of bone fixing system 100 that provides a hinged closing mechanism offset from ligature 14 that also does not require a rod, and which can provide certain advantages over other embodiments. FIG. 26 shows blocking body 120 with first portion 170 hingedly connected via hinge pin 178 to second portion 180. Compression member 140 is an integral part of second portion 180 and is located on the side of second portion 180 directed towards first portion 170. In alternative embodiments, compression member 140 is an integral part of first portion 170 and is located on the side of first portion 170 directed towards second portion 180. Conformable ligature 14 can pass through loop passage 126 in first portion 180 of blocking body 120 to form a loop extending from first portion 180 of blocking body 120, further passed through a passage formed between first surface 146 of compression member 140 and inner surface 125 of blocking body 120, and then passed through exit passage 128 in second portion 170. As with every embodiment described, ligature 14 may get to this desired configuration (with a loop portion extending from blocking body 120) in a variety of ways. An advantage to this embodiment is the low profile possible due to the configuration of closure member 130 offset from compression member 140.

In various embodiments, hinge pin 178 connects first portion 170 to second portion 180 in either a permanent manner or alternatively the hinged connection may be disconnectable. The hinged connection can be formed so as to allow two-way hinged motion for engaging or disengaging first portion 170 from second portion 180. In an alternative embodiment, the hinged connection may allow one-way hinged motion for engaging first portion 170 from second portion 180 but may subsequently prevent first portion 170 from disengaging second portion 180. In various embodiments, first portion 170 and/or second portion 180 may allow hinged motion between a selected arclength, for example, first portion 170 and second portion 180 may move through an arc of approximately 180 degrees.

As further shown in FIGS. 26-28, closure member 130 will be used to close the hinged bone fixing system 100 in a manner to hold ligature 14 in a relatively or completely stable position relative to blocking body 120. Closure member 130 of FIG. 27 is shown having external threads 132 for engaging internal threads 122 in engagement portion 123 of blocking body 120. Second portion 180 may include engagement portion 122 for engagement by threads 132 on closure member 130. In one embodiment, closure member 130 may be positioned within first portion 170 such that closure member 130 is free to rotate in first portion 170 to join first portion 170 with second portion 180, but may not be removed from first portion 170 after such engagement. In other words, in some embodiments, closure member 130 may be rotated to engage threads on closure member 130 with engagement portion 123 to collapse first portion 170 and second portion 180, and the direction of rotation may be reversed to disengage closure member 130 from engagement portion 123, but closure member 130 may not be removed from first portion 170. In the embodiment shown in FIG. 26, closure member 130 can be rotatably positioned in second portion 180 such that closure member 130 is free to rotate in second portion 180 but may not be removed from second portion 180, which can provide the advantage of reducing the risk of having loose hardware (which can be lost inside a patient during surgery) associated with bone fixing system 100.

FIG. 27 depicts a cross-sectional side view of a portion of the embodiment of bone fixing system 100 depicted in FIG. 26, in which conformable ligature 14 may be passed through loop passage 126 in first portion 170 to form a loop extending from first portion 170 of blocking body 120, passed through a passage formed by first surface 146 of compression member 140 and inner surface 125 of blocking body 120, and extend from exit passage 128 in second portion 180. As shown in FIG. 27, first portion 170 and second portion 180 rotate about hinge pin 178 to open or close blocking body 120. Tool portion 134 on closure member 130 may be rotated so threads 132 on closure member 130 engage threads 122 in engagement portion 123. Once bottom surface 135 of closure member 130 reaches a selected point, first portion 170 and second portion 180 compress to impinge movement of ligature 14 relative to blocking body 120.

First surface 146 of compression member 140 and inner surface 125 of blocking body 120 provide a passageway through blocking body 120. In some embodiments, inner surface 125 may be located on first surface 170 and first surface 146 of compression member 140 may be located on second portion 180 as depicted in FIG. 27. In some embodiments, inner surface 125 may be located on second surface 180 and first surface 146 of compression member 140 may be located on first portion 170.

Closure member 130 may be offset from compression member 140 such that threaded engagement of threads 132 of closure member 130 with engagement portion 123 of blocking body 120 may indirectly apply compression to compression member 130. In other words, compression member 140 may be positioned some distance $L_b$ from hinge pin 178 and closure member 130 may be positioned some distance $L_s$ from hinge pin 178. Compression of compression member 140 onto conformable ligature 14 may not be accomplished by directly contacting bottom surface 135 of closure member 130, but may instead be accomplished by rotatably engaging threads 132 with threads 122 to advance closure member 130 in blocking body 120 such that second portion 180 may be leveraged around the fulcrum created by hinge pin 178. An advantage to one embodiment uses the mechanical advantage of $L_s/L_b$ to apply compression forces on conformable ligature 14. Another advantage to one embodiment is the ability for the surgeon to apply large compression forces to conformable ligature 14 due to the mechanical advantage based on the position of hinge pin 178, compression member 140, and closure member 130. The compression forces available may also be based on the radius of curvature of compression member 140, the size or pitch of threads 132 and 122, and/or the size of hinge pin 178. Another advantage may be the precision in which a friction coefficient may be selected between conformable ligature 14 and blocking body 120. In some embodiments, the pitch, shank diameter, or other dimensions of closure member 130 may enable control of the application of compression. For example, a large number of threads per inch may allow more compression due to the mechanical advantage of threads 122 engaging with threads 132, and the application may be more controlled due to the greater angular rotation needed to advance closure member 130 the same distance as closure members 130 having lower numbers of threads per inch. Another advantage to this embodiment relates to the outer surface of first portion 170 and/or second portion 180. Because blocking body 120 can achieve a mechanical advantage through the use of hinge pin 178, closure member 130 may be made smaller than prior art approaches, which allows blocking body 120 to have a smaller opening 123. As shown in FIG. 27, second portion 180 has an outer surface that is curved, which may reduce pain, discomfort, or other undesirable effects that result from using an angular implant.

FIG. 28 depicts a perspective view of the embodiment of FIGS. 26 and 27 shown in a closed configuration, where ligature 14 is held completely or substantially in place relative to blocking body 120. One advantage to this type of embodiment may be the ability to pass conformable ligature 14 around one or more bones, tendons, muscles, rods, plates, screws, or other structures in the body, pass conformable ligature 14 through blocking body 120 out a single exit passage 128, and engage closure member 130 on blocking body 120, but offset from conformable ligature 14 and/or compression member 140. One advantage may be that tensioning tool 250 may not need passage 152 in distal end 154 because closure member 130 (e.g., tool portions 134) may be accessed outside tensioning tool 250.

It should be understood that the various closure mechanisms, closure members, exit passages, and blocking bodies, and other design features shown in the various embodiments of bone fixing system 100 of FIGS. 14-28 may potentially be used in the other embodiments of FIGS. 14-28. For example, the ring-style closure member 130 of the FIG. 25 embodiment can be used on the embodiment of FIG. 22 by modifying the blocking body of FIG. 22 to have external threads onto which the internal threads of the ring-style closure member 130 would engage.

FIGS. 29-38 depict embodiments of bone fixing system 100 in various configurations, arrangements and orientations. In FIGS. 29-38, the embodiment of blocking body 120 is the embodiment depicted in FIGS. 26-28. However, any of the embodiments depicted in FIGS. 14-28 and variations may be used without departing in scope from the present disclosure.

Figures 29, 30:
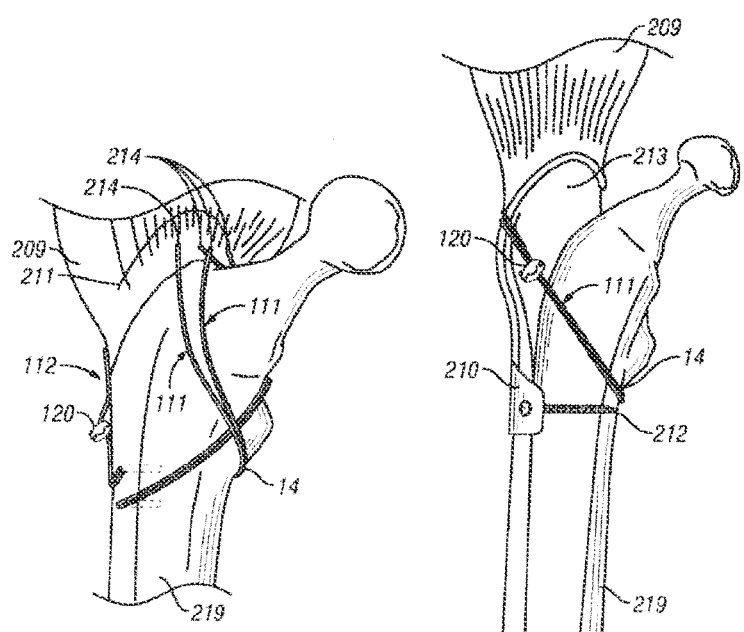
FIG. 29 depicts a perspective view of one embodiment of a bone fixing system attached to a portion of bone.
FIG. 30 depicts a posterior view of one embodiment of a bone fixing system attached to a portion of a bone.

FIG. 29 depicts a perspective view of one embodiment of bone fixing system 100 for holding a bone in a position. Bone fixing system 100 may be useful for orthopedic applications, such as holding a bone near a tendon or muscle. Portions 214 of conformable ligature 14 may be passed through or around a portion of a muscle and through or around a portion of a femur to provide support while a tear or cut in the muscle heals. Advantageously, blocking body 120 may be positioned at various locations near the muscle, tendon, or bone based on the type or extent of the injury, trauma, or illness, surgical preferences such as MIS access, or patient health such as age or weight, or the like. Advantageously, embodiments of bone fixing system 100 may be implanted near other surgical implants without affecting their placement or function. In various embodiments, bone fixing system 100 may include blocking body 120 indirectly applying tension to conformable ligature 14. For example, in the embodiment depicted in FIG. 29, bone fixing system 100 may be implanted to maintain bone 219 in a position with muscle 209 while wound 211 heals. In this embodiment, conformable ligature 14 may be passed around bone 219 and through muscle 209, and through blocking body 120 located on portion 112 of conformable ligature 14 such that substantially all tension between muscle 209 and bone 219 may be supported by portion 111 of conformable ligature 14.

Bone fixing systems 100 may be implanted without affecting plates, rods, or other implanted structures. Bone fixing systems may be implanted without affecting bone screws, hooks, bolts, or other implanted hardware. FIG. 30 depicts one embodiment of conformable ligature 14 passed around a part of bone 219, muscle 209 and/or tendon 213 and through blocking body 120, and further depicts bone screw 212 and plate 210 implanted on a portion of bone 219. In this type of embodiment, bone fixing system 100 including blocking body 120 may be positioned on portion 111 of conformable ligature 14 such that some of the tension between muscle 209 and bone 219 may be supported by blocking body 120.

Figure 31:
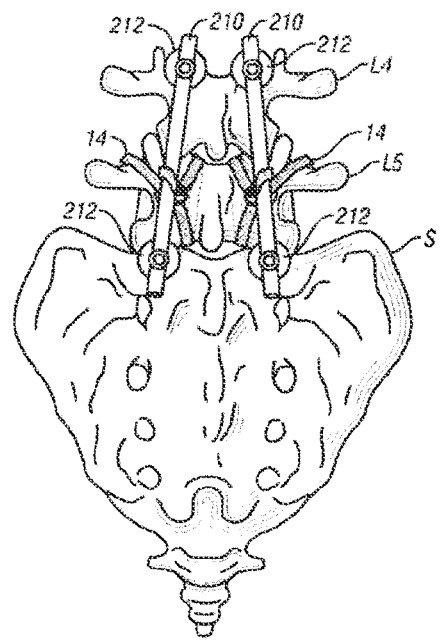
FIG. 31 depicts a sagittal view of one embodiment attached to a portion of a spine, illustrating a method for repairing a spine.
Figure 32:
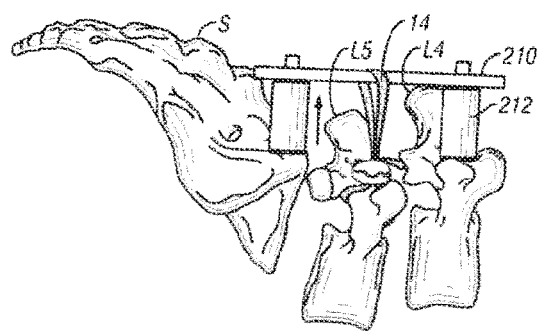
FIGS. 32-38 depict views of a bone fixing system implanted on a spine.

Bone fixing system 100 may be advantageous for correcting alignment of one or more bones. Conformable ligatures 14 and blocking bodies 120 may be useful for correcting alignment of a portion of the spine. FIGS. 31 and 32 depict posterior and sagittal views of a portion of the spine in which bone fixing system 100 may be useful for aligning vertebra L5 with adjacent vertebrae L4 and sacrum S. In some embodiments, bone fastener assemblies 212 may be implanted in lumbar vertebra L4 and sacrum S. In some embodiments, bone fastener assemblies 212 may be inserted through an incision in the skin and implanted using Minimally Invasive Surgery (MIS) techniques, rods 210 may be connected to bone fastener assemblies 212, and ligature 14 may be passed around rods 210. Also shown in FIGS. 31 and 32, ligature 14 may be passed around rods 210 and vertebra such as L5. An advantage to bone fixing system 100 is that the placement of blocking body 120 may not depend on the availability of rod 210. For example, in FIG. 32, the placement of blocking body 120 is not directly over vertebra L5.

Figure 33:
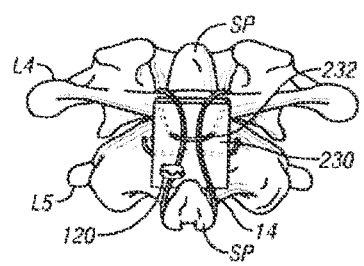

In some embodiments, passing may include going into, through, or out of a structure. In some embodiments, passing may include going over, under, or around a structure. In some embodiments, passing may include crossing over other ligatures 14 or portions of ligatures 14. In some embodiments, passing may include multiple passes along the same path. FIGS. 33-38 depict various embodiments of bone fixing systems in place on a portion of a spine. In FIGS. 33-38, bone fixing system 100 is shown holding bone graft 230, which may be useful for supporting a portion of the spine. However, embodiments of bone fixing system 100 may be used to correct problems with the spine without rods, bone grafts, plates, or other implants. Conformable ligature 14 may be passed around a portion of a bone, such as spinous process SP. Conformable ligature 14 may be passed around a portion of bone graft 230. Passing conformable ligature 14 around a portion of bone graft 230 may include passing a portion of conformable ligature 14 through a portion of bone graft 230. One end of conformable ligature 14 may be inserted and passed through blocking body 120 from one side and the other end of conformable ligature 14 may be inserted and passed through blocking body 120 from another side, as depicted in FIG. 33.

Figure 34:
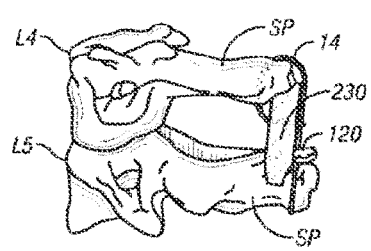
Figure 35:
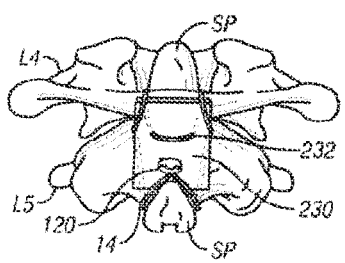
Figure 36:
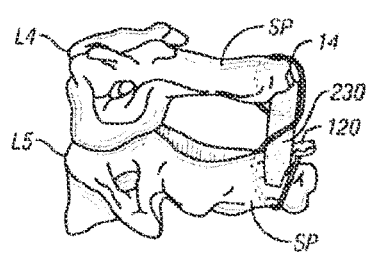
Figure 37:
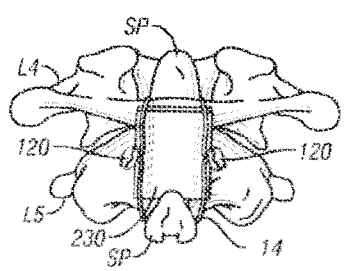
Figure 38:
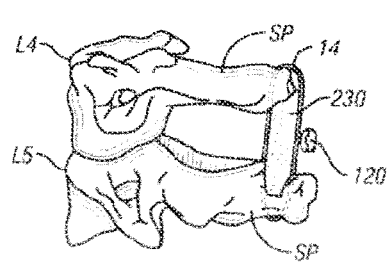

Advantageously, conformable ligature 14 may be selectively passed around structures such as bones and bone grafts. Conformable ligature 14 may be passed around a bone, bone graft, tendon, or other tissue due to disease, injury, tumor, degenerative effects or the like. For example, FIG. 33 depicts a posterior view of one embodiment in which conformable ligature 14 may be passed around a portion of spinous process SP on lower vertebra L5. FIG. 33 further depicts one embodiment in which conformable ligature may be passed through bone, such as the pedicle of lower vertebra L5. As another example, FIG. 34 depicts a sagittal view of one embodiment in which conformable ligature 14 may be passed around the posterior portion of spinous process SP. As another example, FIG. 35 depicts a posterior view of one embodiment in which conformable ligature 14 may be passed around a portion of the pedicle portion of lower vertebra L5. As another example, FIG. 36 depicts a sagittal view of one embodiment in which conformable ligature 14 may be passed around the pedicle portion and the posterior portion of spinous process SP. In some embodiments, ligature 14 may not be passed around a structure. FIG. 37 depicts a posterior view of one embodiment in which conformable ligature 14 may be passed around a portion of the pedicle portion of lower vertebra L5 and the transverse process of upper vertebra L4 but not the spinous process for either vertebra. FIG. 38 depicts a sagittal view of one embodiment in which conformable ligature 14 may be passed around the pedicle portion and through the posterior portion of spinous process SP on lower vertebra L5.

In some embodiments, the surgeon may pass conformable ligature 14 alternative ways due to disease, injury, tumor, degenerative effects or the like. For example, FIG. 33 depicts a posterior view of one embodiment in which conformable ligature 14 may be passed through a portion of the pedicle of lower vertebra L5, which may allow system 100 to apply direct tension on lower vertebra L5. As another example, FIG. 34 depicts a sagittal view of one embodiment in which conformable ligature 14 may be passed around bone graft 230 and spinous process SP on lower vertebra L5 such that the lower portion of bone graft 230 may be prevented from moving posterior to the spine but may move anterior to the spine. FIG. 35 depicts a posterior view of one embodiment in which conformable ligature 14 may be passed around a portion of the pedicle portion of lower vertebra L5, which may allow system 100 to indirectly apply tension on lower vertebra L5. FIG. 36 depicts a sagittal view of one embodiment in which conformable ligature 14 may be passed around bone graft 230 and spinous process SP on lower vertebra L5 such that the lower portion of bone graft 230 may be prevented from moving posterior or anterior to the spine. FIG. 37 depicts a posterior view of one embodiment in which first and second conformable ligatures 110 may be passed around a portion of the pedicle portion of lower vertebra L5. Advantageously, the system 100 may be able to selectively apply tension to either side of the spine. Furthermore, system 100 may be able to control movement between vertebrae L4 and L5 similarly to the embodiments depicted in FIGS. 33 and 34, but without contacting the spinous process SP of lower vertebra L5. FIG. 38 depicts a sagittal view of one embodiment in which conformable ligature 14 may be passed around the pedicle portion and through the posterior portion of spinous process SP on lower vertebra L5. Advantageously, vertebrae L4 and L5 may be able to move relative to each other but bone graft 230 may be held in place.

An advantage to bone fixing system 100 is that the position of blocking body 120 may be based on disease, injury, tumor, degenerative effects or the like. For example, FIG. 33 depicts one embodiment in which a single blocking body 120 may be positioned off-center of the spine. As another example, FIG. 34 depicts one embodiment in which blocking body 120 may be positioned abutting a bone such as spinous process SP. FIG. 35 depicts one embodiment in which blocking body 120 may be positioned centered on the midline of the spine. FIG. 36 depicts one embodiment in which blocking body 120 may be positioned some distance away from spinous process SP. FIG. 37 depicts one embodiment in which two blocking bodies 120 may be positioned lateral to bone graft 230. FIG. 38 depicts one embodiment in which blocking body 120 may be positioned centered between spinous processes SP.

Two or more conformable ligatures 14 and/or two or more blocking bodies 120 may be used to hold a bone, bone graft, tendon, rod, shaft, or other structure in a body. FIG. 36 depicts a posterior view and FIG. 37 depicts a sagittal view of one embodiment of a bone fixing system having two blocking bodies 120 and 120' and two conformable ligatures 14 and 14'. In some embodiments, bone fixing system 100 may include a first conformable ligature 14 passed around a bone such as transverse process TP on lumbar vertebra L4 and transverse process TP on lumbar vertebra L5, and a second conformable ligature 14' passed around a bone such as transverse process TP on lumbar vertebra L4 and transverse process TP on lumbar vertebra L5. Bone fixing system 100 with a first blocking body 120 on a first side of the spine and a second blocking body 120' on the second side of the spine may be used to straighten a spine. For example, tensioning one conformable ligature 14 greater than conformable ligature 14' may bias vertebrae to help straighten a curved spine.

Figure 39:
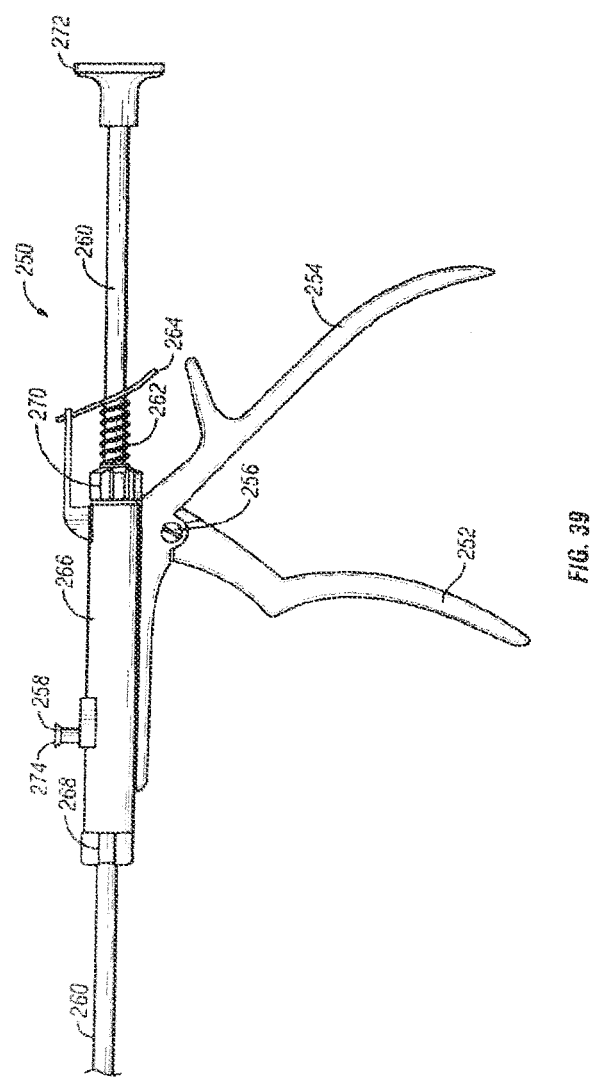
FIG. 39 depicts a side view of one embodiment of a tensioning tool for a bone fixing system.

FIG. 39 depicts a side view of a portion of one embodiment of tensioning tool 250, which may be used to apply tension to conformable ligature 14. As shown in FIG. 39, tensioning tool 250 includes tool body 266 for engaging conformable ligature 14, longitudinal member 260 for advancement in tool body 266, and distal end (such as distal end 154 depicted in FIGS. 14, 17, and 20) for engagement with blocking body 120. As shown in FIG. 39, tool body 266 includes attachment point 274 (with flange 258) for connection to ligature 14, fixed handle 254, movable handle 252 for rotation about axis 256, return spring 262, catch mechanism 264, return spring adjustment member 270, and spring adjustment member 268.

Attachment point 274 can attach first and second ends of conformable ligature 14 to tensioning tool 250. In some embodiments, attachment point 274 may include flange 258 for preventing first and second ends of conformable ligature 14 from detaching from tensioning tool 250. Distal end 154 (such as the embodiments shown in FIGS. 14, 17, and 20) of tensioning tool 250 may engage to a portion of blocking body 120. Fixed handle 254 may be gripped by a surgeon, movable handle 252 may be rotated about axis 256, such as by squeezing movable handle 252, to longitudinal member 260 through tool body 266 a selected distance. Advancing longitudinal member 260 to move blocking body 120 away from tool body 266 while maintaining first and second ends of conformable ligature 14 on attachment point 274 applies tension to conformable ligature 14. In some embodiments, the selected distance longitudinal member 260 advances through tool body 266 may be proportional to the tension applied to conformable member 110.

In some embodiments, tool body 266 may include return spring 262, catch mechanism 264, and return spring adjustment member 270 for controlling the distance that longitudinal member 260 is allowed to return when movable handle 252 is released. In some embodiments, return spring 262 may bias catch mechanism 264 such that movement is permitted in one direction only. In some embodiments, return spring 262 may bias catch mechanism 264 such that longitudinal member 260 may only move forward through tool body 266. Advantageously, return spring 262 may ensure that a surgeon does not inadvertently relieve tension from conformable ligature 14. In other words, tensioning tool 250 may have a default configuration for tensioning conformable ligature 14. In some embodiments, actuating catch mechanism 264 (such as a surgeon pressing on catch mechanism 264 with a thumb) may change the positioning of catch mechanism 264 such that movement of longitudinal member 260 is permitted in a reverse direction as well. In some embodiments, movement of longitudinal member 260 in a reverse direction may include changing the positioning of catch mechanism 264 in relation to longitudinal member 260 as well as pulling in a reverse direction on grasping member 272.

In some embodiments, tensioning tool 250 may include spring adjustment member 268 for adjusting the compression on a spring (not shown) in body 266. In some embodiments, rotating spring adjustment member 268 one direction, spring adjustment member 268 may be advanced some distance into body 266 such that a spring may be compressed. In some embodiments, rotating spring adjustment member 268 in the other direction, spring adjustment member 268 may be advanced some distance out of body 266 such that compression forces on the spring may be relieved. By changing the compression forces on the spring, the spring may exert more or less force on longitudinal member 260, which may affect how much tension can be applied to the ends of conformable ligature 14.

In some embodiments, ligature 14 may be passed around elongate members 210, bone fastener assemblies 212, vertebrae (such as L5), and other tendons, muscles, plates or other anatomical or implanted structures and the ends of ligature 14 may be passed into a portion of blocking body 120, such that a loop is formed extending from a first portion of blocking body 120. In some embodiments, first and second ends of ligature 14 may be passed through a passage in blocking body 120. In some embodiments, a passage may be formed by inner surface 125 of blocking body 120 and first surface 146 of compression member 140. In some embodiments, first and second ends of ligature 14 may exit by passing out of one or more exit passages 128 in blocking body 120.

Distal end 154 of tensioning tool 250 engages blocking body 120. In some embodiments, distal end 154 of longitudinal member 260 may conform to the shape or profile of blocking body 120. In some embodiments, distal end 154 of longitudinal member 260 may be configured with features for engaging one or more features on blocking body 120. In some embodiments, first and/or second ends of ligature 14 may be attached to tensioning tool 250. In some embodiments, first and/or second ends of ligature 14 may be attached to attachment point 274 located on tool body 266. In some embodiments, movable handle 252 of tensioning tool 250 may be rotated about axis 256 to advance longitudinal member 260 through tool body 266. The advancement of longitudinal member 260 through tensioning tool 250 moves attachment point 274 away from blocking body 120, pulling ends of ligature 14 to decrease the size of the loop, and further advancement tensions ligature 14. In some embodiments, the tension applied to ligature 14 may be sufficient to hold one or more structures in a desired position. In some embodiments, the tension applied to ligature 14 may be sufficient to hold a bone in a position. In some embodiments, the tension applied to ligature 14 may be sufficient to pull one or more bones or structures into alignment. For example, tensioning tool 250 may provide sufficient tension to one or more ends of ligatures 14 (depicted in FIG. 31) to pull vertebra L5 (depicted in FIG. 32) in alignment with the natural curvature of the spine.

In some embodiments, once an appropriate tension has been applied to ligature 14, closure member 130 may be actuated to create a friction force to restrict movement of ligature 14 relative to blocking body 120, or to impinge ligature 14 in blocking body 120. In some embodiments, closure member 130 may be pre-installed in blocking body 120. In some embodiments, closure member 130 may be inserted in blocking body 120 after engagement of blocking body 120 by tensioning tool 250. In some embodiments, closure member 130 may be inserted through distal end 154 of longitudinal member 260 into blocking body 120.

In some embodiments, once closure member 130 has engaged threads 122 in blocking body 120 to provide a desired friction force to impinge ligature 14 in blocking body 120, first and second ends of ligature 14 may be disconnected from tensioning tool 250. Once ligature 14 has been disconnected from tensioning tool 250, tensioning tool 250 may be disengaged from blocking body 120.

The foregoing specification and accompanying figures are for the purpose of teaching those skilled in the art the manner of carrying out the disclosure and should be regarded in an illustrative rather than a restrictive sense. As one skilled in the art can appreciate, embodiments disclosed herein can be modified or otherwise implemented in many ways without departing from the spirit and scope of the disclosure and all such modifications and implementations are intended to be included within the scope of the disclosure as set forth in the claims below.

What is claimed is:

1. A method for engaging a bone, comprising:
providing a clamping body having a loop passage passing through a first exterior surface and an exit passage passing through a second exterior surface different from the first exterior surface, and a conformable ligature having a first end, a first end portion extending from the first end to a first loop portion, a second end, and a second end portion extending from the second end to a second loop portion;
positioning the first end portion and the second end portion of the conformable ligature through the clamping body such that the first loop portion and the second loop portion extend from the loop passage of the clamping body to form a loop between the first end portion of the conformable ligature and the second end portion of the conformable ligature, at least one of the first end and the second end of the conformable ligature extending from the exit passage of the clamping body; and
engaging a locking member with an engagement portion of the clamping body to press the first end portion of the flexible ligature against the second end portion of the flexible ligature within the clamping body to prevent significant movement of the conformable ligature relative to the clamping body without securing the conformable ligature against a spinal rod.

2. A method according to claim 1, further comprising tensioning the at least one of the first end and the second end of the conformable ligature to tension the loop of the conformable ligature around a bony structure.

3. A method according to claim 1, further comprising passing the loop of the conformable ligature around a bony element.

4. A method according to claim 3, further comprising tensioning the conformable ligature relative to the clamping body.

5. A method according to claim 1, wherein the locking member comprises a screw and wherein engaging the locking member with the engagement portion of the clamping body further comprises threading the screw relative to the engagement portion of the clamping body.

6. A method according to claim 5, wherein tightening the screw causes the clamping body to create a force against the conformable ligature.

7. A method according to claim 6, wherein the force against the conformable ligature prevents any additional portion of the conformable ligature from becoming part of the loop, thereby defining a size of the loop.

8. A method according to claim 1, wherein significant movement is all movement.

9. A method of engaging a bone, comprising:
positioning a loop portion of a flexible ligature around a bony structure with a first end portion and a second end portion of the flexible ligature extending through a passage of a clamping member with the loop portion extending from a first opening of the clamping member in a first direction, the first end portion of the flexible ligature extending from the loop portion to a first end of the flexible ligature and the second end portion of the flexible ligature extending from the loop portion to a second end of the flexible ligature;

wherein the first end and the second end both extend from a second opening of the clamping member in a second direction different from the first direction;

applying tension to the flexible ligature to draw the loop portion of the flexible ligature against the bony structure; and engaging a screw in a threaded bore of the clamping body to press the first end portion of the flexible ligature against the second end portion of the flexible ligature within the clamping body to secure the conformable ligature relative to the clamping body without securing the conformable ligature against a spinal rod.

10. The method of claim 9, wherein engaging the screw in the threaded bore of the clamping body presses the first end portion of the flexible ligature against a surface of the passage through the clamping member.

11. The method of claim 9, wherein applying tension to the flexible ligature includes drawing the first end and/or the second end of the flexible ligature away from the clamping body.

* * * * *